United States Patent
Brünner et al.

(10) Patent No.: US 6,224,865 B1
(45) Date of Patent: May 1, 2001

(54) SUPPRESSION OF INHIBITORS

(75) Inventors: Nils Brünner, Hellerup; John Rømer, Copenhagen, both of (DK); Vincent Ellis, Woodford Green (GB); Charles Pyke, Hillerød (DK); Jan Grøndahl-Hansen, Holte (DK); Helle Pedersen, Allerød (DK); Heine Høi Hansen, Holte (DK); Keld Danø, Charlottenlund (DK)

(73) Assignee: Cancerforskningsfonden AF 1989, Copenhagen K (DK)

( * ) Notice: Subject to any disclaimer, the term of this patent is extended or adjusted under 35 U.S.C. 154(b) by 0 days.

(21) Appl. No.: 08/583,129

(22) PCT Filed: Jul. 18, 1994

(86) PCT No.: PCT/DK94/00288

§ 371 Date: May 15, 1996

§ 102(e) Date: May 15, 1996

(87) PCT Pub. No.: WO95/02413

PCT Pub. Date: Jan. 26, 1995

(30) Foreign Application Priority Data

Jul. 16, 1993 (DK) .................................................. 0851/93

(51) Int. Cl.$^7$ ......................... A61K 39/395; A01N 37/18

(52) U.S. Cl. ................................. 424/130.1; 421/138.1; 421/141.1; 421/145.1; 421/155.1; 421/152.1; 421/158.1; 421/172.1; 421/179.1; 421/181.1; 421/183.1; 514/2

(58) Field of Search .............................. 424/152.1, 141.1, 424/145.1, 155.1, 130.1, 138.1, 158.1, 172.1, 179.1, 181.1, 183.1; 514/2

(56) References Cited

U.S. PATENT DOCUMENTS 4,906,457 * 3/1990 Ryan ........................................ 424/59
5,800,814 9/1998 Fusek et al. .

FOREIGN PATENT DOCUMENTS

8700549 * 1/1987 (WO) .
WO 93/17715 * 9/1993 (WO) .
9404512 3/1994 (WO) .
9532190 11/1995 (WO) .
9742973 11/1997 (WO) .

OTHER PUBLICATIONS

Hang et al (Fibrinolysis & Proeolysis, 12:145–154), 1998.*
Tjuvajev et al (Proc. AACR, 36, p. A557), 1995.*
Gura (Science, 278:1041–1042), 1997.*
Osband et al, Immunol. Today, 11:193–195, 1990.*
Hird et al, in "Genes and Cancer" Carney et al, Ed, John Wiley & Sons Ltd, 1990, pp. 83–89.*
Girondahl–Hansen et al (Can. Res. 1993, 53:2513–2521).*
Foucre et al (Brit J. Can, 1991, 64:926–932.*

Tsuchiya, et al., *The Antibody to Plasminogen Activator Inhibitor–1 Suppresses Pulmonary Metastases of Human Fibrosarcoma in Athymic Mice*, Gen. Diagn. Pathol., vol. 141, pp. 41–48, 1995.

Bajou, et al., *Importance of Host Plasminogen Activator Inhibitor–1 During Cancer Invasion*, Draft manuscript.

Charlton, et al., *XR5118, a novel modulator of plasminogen activatory inhibitor–1 (PAI–1), increases endogenous tPA activity in the rat*, Fibrinolysis & Proteolysis, vol. 11, pp. 51–56, 1997.

Friederich, et al., *Novel Low–Molecular–Weight Inhibitor of PAI–1 (XR5118) Promotes Endogenous Fibrinolysis and Reduces Postthrombolysis Thrombus Growth in Rabbits*, Circulation, vol. 96, No. 3, pp. 916–921, Aug. 5, 1997.

Carmeliet, et al., *Plasminogen Activator Inhibitor–1 Gene–deficient Mice*, J. Clin. Invest., vol. 92, pp. 2756–2760, Dec. 1993.

Carmeliet, et al., *Plasminogen Activator Inhibitor–1 Gene–deficient Mice*, J. Clin. Invest., vol. 92, pp. 2746–2755, Dec. 1993.

Fay, et al., *Human Plasminogen Activator Inhibitor–1 (PAI–1) Deficiency: Characterization of a Large Kindred With a Null Mutation in the PAI–1 Gene*, Blood, vol. 90, No. 1, pp. 204–208, Jul. 1, 1997.

Baum, et al., *Clinical Course of Ovarian Cancer Patients Under Repeated Stimulation of HAMA Using Mab OC125 and B43.13*, Hybridoma, vol. 12, No. 5, pp. 583–589, 1993.

Baum, et al., *Activating Anti–Idiotypic Human Anti–Mouse Antibodies for Immunotherapy of Ovarian Carcinoma*, Cancer, vol. 73, No. 3, pp. 1121–1125, Feb. 1, 1994.

Madiyalakan, et al., *Antiidiotype Induciton Therapy: Evidence for the Induction of Immune Response through the Idiotype Network in Patients with Ovarian Cancer after Administration of Anti–CA125 Murine Monoclonal Antibody B43.13*, Hybridoma, vol. 14, No. 2, pp. 199–203, 1995.

Donnerstag, et al., *Evaluation of Tumor Immunity in Patients with Ovarian Cancer after Immunoscintigraphy in a Long–Term Follow–up*, Hybridoma, vol. 14, No. 2, pp. 191–197, 1995.

(List continued on next page.)

Primary Examiner—Susan Ungar
(74) Attorney, Agent, or Firm—Iver P. Cooper

(57) ABSTRACT

The present invention relates to methods for inhibiting malignant tumour growth, invasion and/or metastasis in a patient, the method comprising suppressing the inhibitory activity of an inhibitor of a protease or of a non-proteolytic matrix-degrading enzyme (IPNME) in malignant tumour tissue or potential malignant tumour tissue. The suppression may be brought about by administering compounds interacting with the IPNME, but also administration of compounds interacting with transcription of genes encoding the IPNME is a possibility. The invention also relates to methods of selecting and identifying compounds in the therapeutical methods, as well of the use of such compounds in the treatment of malignancies.

24 Claims, 7 Drawing Sheets

OTHER PUBLICATIONS

Noujaim, et al., *Monoclonal antibody B43.13 for immunoscintigraphy and immunotherapy of ovarian cancer*, Reprint from Current Tumor Diagnosis: Applications Clinical Relevance Research—Trends, 7th Symposium on Tumor Markers, Hamburg 1993, pp. 823–829.

Baselga, et al., *Recombinant Humanized Anti–HER2 Antibody (Herceptin™) Enhances the Antitumor Activity of Paclitaxel and Doxorubicin against HER2/new Overexpressing Human Breast Cancer Xenografts*, Cancer Research, vol. 58, pp. 2825–2830, Jul. 1, 1998.

Pegram, et al., *Phase II Study of Receptor–Enhanced Chemosensitivity Using Recombinant Humanized Anti–p185$^{HER2/neu}$ Monoclonal Antibody Plus Cisplatin in Patients with HER2/neu–Overexpressing Metastatic Breast Cancer Refractory to Chemotherapy Treatment*, Journal of Clinical Oncology, vol. 16, No. 8, pp. 2659–2671, Aug. 1998.

Grondahl–Hansen, et al., *Plasminogen Activator Inhibitor Type 1 in Cytosolic Tumor Extracts Predicts Prognosis in Low–Risk Breast Cancer Patients*, Clinical Cancer Research, vol. 3, pp. 233–239, Feb. 1997.

Pedersen, et al., *The complex between urokinase plasminogen activator and its type–1 inhibitor in breast cancer extracts quantitated by ELISA*, Journal of Immunological Methods, vol. 203, pp. 55–65, 1997.

Nielsen, et al., *Association between plasma concentrations of plasminogen activator inhibitor–1 and survival in patients with colorectal cancer*, BMJ, vol. 316, pp. 829–830, 1998.

Pedersen, et al., *Determination of the Complex between Urokinase and Its Type–1 Inhibitor in Plasma from Healthy Donors and Breast Cancer Patients*, Clinical Chemistry, vol. 45, pp. 1206–1213, 1999.

Konno, et al., Antitumor Effect of a Neutralizing Antibody to Vascular Endothelial Growth Factor on Liver Metastasis of Endocrine Neoplasm, *Jpn. J. Cancer Res.*, vol. 89, pp. 933–939, Sep. 1998.

Schnurch, et al., Growth Inhibition of Xenotransplanted Human Carcinomas by a Monoclonal Antibody Directed Against the Epidermal Growth Factor Receptor, *European Journal of Cancer*, vol. 30A, No. 4, pp. 491–496, 1994.

Kanai, et al., *Anti–Tumor and Anti–Metastatic Effect of Human–Vascular–Endothelial– Growth–Factor–Neutralizing Antibody on Human Colon and Gastric Carcinoma Xenotransplanted Orthotopically into Nude Mice*, Int. J. Cancer, vol. 77, pp. 933–936, 1998.

Tosi, et al., *Anti–Tumor Efficacy of an Anti–Epidermal–Growth–Factor–Receptor Monoclonal Antibody and its $F(ab')_2$ Fragment Against High– and Low–EGRF–Expressing Carcinomas in Nude Mice*, Int. J. Cancer, vol. 62, pp. 643–650, 1995.

Debrock et al., *Neutralization of plasminogen activator inhibitor–1 inhibitory properties: identification of two different mechanisms*, Biochimica et Biophysics Acta., vol. 1337, pp. 257–266, 1997.

Andreasen, P.A., et al., "Plasminogen Activator Inhibitors: Hormonally Regulated Serpins," *Molecular and Cellular Endocrinology* 68:1–19 (1990).

Aqvist, J., et al., "A New Method for Predicting Binding Affinity in Computer–aided Drug Design," *Protein Engineering* 7(3):385–391 (1994).

Barbas III, C.F., et al., "Assembly of Combinational Antibody Libraries on Phage Surfaces: The Gene III Site," *Proc. Natl. Acad. Sci. USA* 88:7978–7982 (1991).

Basset, P., et al., "A Novel Metalloproteinase Gene Specifically Expressed in Stromal Cells of Breast Carcinomas," *Nature* 348:699–704 (1990).

Basset, P., et al., "Expression of the Stromelysini–3 Gene in Firbroblastic Cells of Invasive Carcinomas of the Breast and Other human Tissues: A Review," *Breast Cancer Research and Treatment* 24:185–193 (1993).

Behrendt, N., et al., "The Human Receptor for Urokinase Plasminogen Activator," *The Journal of Biological Chemistry* 265(11):6453–6460 (1990).

Behrendt, N., et al., "The Ligand–binding Domain of the Cell Surface Receptor for Urokinase–type Plasminogen Activator," *The Journal of Biological Chemistry* 266(12):7842–7847 (1991).

Brunner, N., et al., "lacZ Transduced Human Breast Cancer Xenografts as an in vivo Model for the Study of Invasion and Metastasis," *Eur. J. Cancer* 28A(12):1989–1995 (1992).

Brunner, N., et al., "The Nude Mouse as an in vivo Model for Human Breast Cancer Invasion and Metastasis," *Breast Cancer Research and Treatment* 24:257–264 (1993).

Campbell, P.G., et al., "Involvement of the Plasmin System in Dissociation of the Insulin–Like Growth Factor–Binding Protein Complex," *Endocrinology* 130(3) 1401–1412 (1992).

Cubellis, M.V., et al., "Binding of Single–chain Prourokinase to the Urokinase Receptor of Human U937 Cells," *The Journal of Biological Chemistry* 261(34):15819–15822 (1986).

Dano, K., et al., "Plasminogen Activators, Tissue Degradation, and Cancer," *Advances in Cancer Research* 44:139–266 (1985).

Dano, K., et al., "The Receptor for Urokinase Plasminogen Activator. Stromal Cell Involvement in Extracellular Proteolysis During Cancer Invasion," *Manuscript for Proteolysis and Protein Turnover* Portland Press, London, pp. 1–14 (1992).

Devlin, J.J., et al., "Random Peptide Libraries: A Soruce of Specific Protein Binding Molecules," *Science* 249:404–406 (1990).

Duffy, M.J., et al., "Urokinase–Plasminogen Activator, A Marker for Aggressive Breast Carcinomas," *Cancer* 62:531–533 (1988).

Duffy, M.J., et al., "Urokinase–Plasminogen Activator, a New Independent Prognostic Marker in Breast Cancer," *Cancer Research* 50:6827–6829 (1990).

Eichler, J., et al., "Identifiction of Substrate–Analog Trypsin through the Screening of Synthetic Peptide Combinatorial Libraries," *Biochemistry* 32:11035–11041 (1993).

Ellis, V., et al., "Inhibition of Receptor–bound Urokinase by Plasminogen–activator Inhibitors," *The Journal of Biological Chemistry* 265(17):9904–9908 (1990).

Ellis, V., et al., "Plasminogen Activation by Receptor–Bound Urokinase," *Seminars in Thrombosis and Hemostasis* 17(3):194–200 (1991).

Ellis, V., et al., "The Urokinase Receptor: Involvement in Cell Surface Proteolysis and Cancer Invasion," *Annals of the New York Academy of Sciences* 667:13–31 (1992).

Estreicher, A, et al., "The Receptor for Urokinase Type Plasminogen Activator Polarizes Expression of the Protease to the Leading Edge of Migrating Monocytes and Promotes Degradation of Enzyme Inhibitor Complexes," *The Journal of Cell Biology* 111:783–792 (1990).

Foekens, J.A., et al., "Prognostic Value of Urokinase–type Plasminogen Activator in 671 Primary Breast Cancer Patients," *Cancer Research* 52:6101–6105 (1992).

Frandsen, T.L., et al., "Assays for the Study of Human Cancer Cell Invasion and Metastasis," *Fibrinolysis* 6(4):71–76 (1992).

Fijuwara, K, et al., "Enzyme–linked Immunosorbent Assay for the Quantification of Actinomycin D Using β–D–Galactosidase as a Label," *Cancer Research* 48:4843–4847 (1988).

Grondahl–Hansen, J., et al., "Localization of Urokinase–type Plasminogen Activator in Stromal Cells in Adenocarcinomas of the Colon in Humans," *American Journal of Pathology* 138(1):111–117 (1991).

Hammer, J., et al., "Identification of a Motif for HLA–DRI Binding Peptides Using M13 Display Libraries," *J. Exp. Med.* 176:1007–1013 (1992).

Hearing, V.J., et al., "Modulation of Metastatic Potential by Cell Surface Urokinase of Murine Melanoma Cells," *Cancer Research* 48:1270–1278 (1988).

Hoyer–Hansen, G., et al., "Urokinase Plamsinogen Activator Cleaves Its Cell Surface Receptor Releasing the Ligand–binding Domain," *The Journal of Biological Chemistry* 267(25):18224–18229 (1992).

Ichinose, A., et al., "The Activation of Pro–urokinase by Plasma Kallikrein and Its Inactivation by Thrombin," *The Journal of Biological Chemistry* 261(8):3486–3489 (1986).

Janicke, F., et al., "Urokinase–type Plasminogen Activator (u–PA) Antigen is a Predictor of Early Relapse in Breast Cancer," *Fibrinolysis* 4:69–78 (1990).

Janicke, F., et al., "Clinical Relevance of the Urokinase–Type and Tissue–Type Plaminogen Activators and of Their Type 1 Inhibitor in Breast Cancer," *Seminars in Thrombosis and Hemostasis* 17(3):303–311 (1991).

Jin, L, et al., "Immunochemical Localization of Heparanase in Mouse and Human Melanomas," *Int. J. Cancer* 45:1088–1095 (1990).

Kang, A.S., et al., "Linkage of Recognition and Replication Functions by Assembling Combinatorial Antibody Fab Libraries Along Phage Surfaces," *Proc. Natl. Acad. Sic. USA* 88:4363–4366 (1991).

Kobayashi, H., et al., "Cathepsin B Efficiently Activates the Soluble and the Tumor Cell Receptor–bound Form of the Proenzyme Urokinase–type Plasminogen Activator (Pro–uPA)," *The Journal of Biological Chemistry* 266(8):5147–5152 (1991).

Kristensen, P., et al., "Plasminogen Activator Inhibitor–type 1 in Lewis Lung Carcinoma," *Histochemistry* 93:559–566 (1990).

Kristensen, P., et al., "Localization of Urokinase–type Plasminogen Activator Messenger RNA in the Normal Mouse by In Situ Hybridization," *The Journal of Histochemistry and Cytochemistry* 39(3):341–349 (1991).

Kristensen, P., et al., "Two Alternatively Spliced Mouse Urikinase Receptor mRNAs with Different Histological Localization in the Gastrointestinal Tract," *The Journal of Cell Biology* 115(6):1763–1771 (1991).

Laiho, M., et al., "Growth Factors in the Regulation of Pericellular Proteolysis: A Review," *Cancer Research* 49:2533–2553 (1991).

Liotta, L.A., "Tumor Invasion and Metastases–Role of the Extracellular Matrix: Rhoads Memorial Award Lecture," *Cancer Research* 46:1–7 (1986).

Liotta, L.A., et al., "Cancer Metastasis and Angiogenesis: An Imbalance of Positive and Negative Regulation," *Cell* 64:327–336 (1991).

Lipford III, E.H., et al., "Prognostic Factors in Surgically Resected Limited–stage, Nonsmall Cell Carcinoma of the Lung," *The American Journal of Surgical Pathology* 8(5):357–365 (1984).

Lund, L.R., et al., "Urokinase Receptor mRNA Level and Gene Transcription Are Strongly and Rapidly Increased by Phorbol Myristate Acetate in Human Monocyte–like U937 Cells," *The Journal of Biological Chemistry* 266(8): 5177–5181 (1991).

Lund, L.R., et al., "Urokinase–Receptor Biosynthesis, mRNA Level and Gene Transcription are Increased by Transforming Growth Factor β1 in Human A549 Lung Carcinoma Cells," *The EMBO Journal* 10(11):3339–3407 (1991).

Lyons, R.M., et al., "Mechanism of Activation of Latent Recombinant Transforming Growth Factor β1 by Plasmin," *The Journal of Cell Biology* 110:1361–1367 (1990).

Marcotte, P.A., et al., "The Matrix Metalloproteinase Pump–1 Catalyzes Formation of Low Molecular Weight (Pro)urokinase in Cultures of Normal Human Kidney Cells," *The Journal of Biological Chemistry* 267(20):13803–13806 (1992).

Mignatti, P., et al., "Tumor Invasion Through the Human Amniotic Membrane: Requirement for a Proteinase Cascade," 47:487–498 (1986).

Mimuro, J., et al., "Purification of a Protein from Bovine Plasma That Binds to Type 1 Plasminogen Activator Inhibitor and Prevents Its Interaction with Extracellular Matrix," *The Journal of Biological Chemistry* 264(2):936–939 (1989).

Moller, L.B., "Structure and Function of the Urokinase Receptor," *Blood Coagulation and Fibrinolysis* 4:293–303 (1993).

Mountain, C.F., et al., "Lung Cancer Classification: The Relationship of Disease Extent and Cell Type to Survival in a Clinical Trials Population," *Journal of Surgical Oncology* 35:147–156 (1987).

Nielsen, L.S., et al., "Enzyme–Linked Immunosorbent Assay for Human Urokinase–Type Plasminogen Activator and its Proenzyme Using a Combination of Monoclonal and Polyclonal Antibodies," *Journal of Immunoassay* 7(3):209–228 (1986).

Nykjaer, A, et al., "Purified $α_2$–Macroglobulin Receptor/ LDL Receptor–related Protein Binds Urokinase: Plasminogen Activator Inhibitor Type–1 Complex," *The Journal of Biological Chemistry* 267(21):14543–14546 (1992).

Ossowksi, L., et al., "Antibodies to Plasmingen Activator Inhibit Human Tumor Metastasis," *Cell* 35:611–619 (1983).

Ossowski, L., "In Vivo Invasion of Modified Chorioallantoic Membrane by Tumor Cells: the Role of Cell Surface–bound Urokinase," *The Journal of Cell Biology* 107:2437–2445 (1988).

Pannekoek, H., et al., "Functional Display of Human Plasminogen–Activtor Inhibitor 1 (PAI–1) on Phages: Novel Perspective for Structure–function Analysis by Error–Prone DNA Synthesis," *Gene* 128:135–140 (1993).

Parmley, S.F., et al., "Antibody–selectable Filaments fd Phage Vectors: Affinity Purification of Target Genes," *Gene* 73:305–318 (1988).

Patthy, L., "Evolution of the Proteases of Blood Coagulation and Fibrinolysis by Assembly from Modules," *Cell* 41:657–663 (1985).

Pepper, M.S., et al., "Plasminogen Activator Inhibitor–1 Is Induced in Migrating Endothelial Cells," *Journal of Cellular Physiology* 153:129–139 (1992).

Ploug, M., et al., "Cellular Receptor for Urokinase Plasminogen Activator," *The Journal of Biological Chemistry* 266(3):1926–1933 (1991).

Pollanen, J., et al., "Ultrastructural Localization of Plasma Membrane–associated Urokinase–type Plasminogen Activator at Focal Contacts," *The Journal of Cell Biology* 106:87–95 (1988).

Poulsom, R., et al., "Stromal Expression of 72 kda Type IV Collagenase (MMP–2) and TIMP–2 mRNAs in Colorectal Neoplasia," *American Journal of Pathology* 141(2):389–396 (1992).

Pyke, C., et al., "Urokinase–type Plasminogen Activator is Expressed in Stromal Cells and its Receptor in Cancer Cells at Invasive Foci in Human Colon Adenocarcinomas," *American Journal of Pathology* 138(5):1059–1067 (1991).

Pyke, C., et al., "The Plasminogen Activation System in Human Colon Cancer: Messenger RNA for the Inhibitor PAI–1 is Located in Endothelial Cells in the Tumor Stroma," *Cancer Research* 51:4067–4071 (1991).

Pyke, C., et al., "Localization of Messenger RNA for $M_r$ 72,000 and 92,000 Type IV Collagenases in Human Skin Cancers by in Situ Hybridization," *Cancer Research* 52:1336–1341 (1992).

Pyke, C., et al., "Receptor for Urokinase is Present in Tumor–associated Macrophages in Ductal Breast Carcinoma," *Cancer Research* 53:1911–1915 (1993).

Pyke, C., et al., "Messenger RNA for Two Type IV Collagenases is Located in Non–Malignant Stromal Cells in Human Colon Cancer," *Amer. J. Pathol.* In press pp. 1–16 (1992).

Quax, P.H.A., et al., "Metastatic Behavior of Human Melanoma Cell Lines in Nude Mice Correlates with Urokinase–type Plasminogen Activator, its Type–1 Inhibitor, and Urokinase–mediated Matrix Degradation," *The Journal of Cell Biology* 115(1):191–199 (1991).

Reich, R., et al., "Effects of Inhibitors of Plasminogen Activator, Serine Proteinases, and Collagenase IV on the Invasion of Basement Membranes by Metastatic Cells," *Cancer Research* 48:3307–3312 (1988).

Reilly, D, et al., "Type–1 Plasminogen Activator Inhibitor in Human Breast Carcinomas," *Int. J. Cancer* 50:208–214 (1992).

Rochefort, H, et al., "Oestrogen–induced pro–cathepsin D in Breast Cancer: From Biology to Clinical Applications," *Proceedings of the Royal Society of Edinburgh* 95B:107–118 (1989).

Roldan, A.L., et al., "Cloning and Expression of the Receptor for Human Urokinase Plasminogen Activator, a Central Molecule in Cell Surface, Plasmin Dependent Proteolysis," *The EMBO Journal* 9(2):467–474 (1990).

Ronne, E., et al., "Cell–induced Potentiation of the Plasminogen Activation System is Abolished by a Monoclonal Antibody that Recognizes the $NH_2$–terminal Domain of the Urokinase Receptor," *FEBS Letters* 288(1,2):233–236 (1991).

Rosenquist, C., et al., "Enzyme–linked Immunosorbent Assay of Urokinase–type Plasminogen Activator (uPA) in Cytosolic Extracts of Human Breast Cancer Tissue," *Breast Cancer Research and Treatment* 28:223–229 (1993).

Saksela, O., et al., "Release of Basic Fibroblast Growth Factor–Heparan Sulfate Complexes from Endothelial Cells by Plasminogen Activator–mediated Protecolytic Activity," *The Journal of Cell Biology* 110:767–775 (1990).

Sappino, A.P., et al., "Differential Protease Expression by Cutaneous Squamous and Basal Cell Carcinomas," *J. Clin. Invest.* 88:1073–1079 (1991).

Sato, Y., et al., "Inhibition of Endothelial Cell Movement by Pericytes and Smooth Muscle Cells: Activation of a Latent Transforming Growth Factor–$\beta$1–like Molecule by Plasmin During co–culture," *The Journal of Cell Biology* 109:309–315 (1989).

Scoot, J.K, "Discovering Peptide Ligands Using Epitope Libraries," *Trends Biochem.* 17:241–245 (1992).

Scott, J.K., et al., "Searching for Peptide Ligands with an Epitope Library," *Science* 249:386–390 (1990).

Scott, R.W., et al., "Protease Nexin," *The Journal of Biological Chemistry* 260(11):7029–7034 (1985).

Skriver, L., et al., "Immunocytochemical Localization of Urokinase–type Plasminogen Activator in Lewis Lung Carcinoma," *The Journal of Cell Biology* 99:752–757 (1984).

Sorensen, J.B., et al., "Prognostic Factors in Resected Stages I and II Adenocarcinoma of the Lung," *J. Thorac Cardiovasc. Surg.* 99:218–226 (1990).

Tryggvason, K., et al., "Proteolytic Degradation of Extracellular Matrix in Tumor Invasion," *Bochimica et Biophysica Acta* 907:191–217 (1987).

Tryggvason, K., et al., "Type IV Collagenases in Invasive Tumors," *Breast Cancer Research and Treatment* 24:209–218 (1993).

Vassalli, J.D., et al., "A Cellular Binding Site for the $M_r$ 55,000 Form of the Human Plasminogen Activator, Urokinase," *The Journal of Cell Biology* 100:86–92 (1985).

Vittoria–Cubellis, M., et al., "Receptor–Mediated Internalization and Degradation of Urokinase is Caused by its Specific Inhibitor PAI–1," *The EMBO Journal* 9(4):1079–1085 (1990).

\* cited by examiner

SUPPRESSION OF INHIBITORS

BRIEF DESCRIPTION OF THE INVENTION

In order to invade and spread, cancer cells must degrade extracellular matrix proteins. This degradation is catalyzed by the concerted action of several enzymes including proteases and non-proteolytic matrix-degrading enzymes e.g. metalloproteases such as interstitial collagenases, type IV collagenases and stromelysins, aspartic proteases such as cathepsin D, other degradative enzymes such as heparanase, and serine proteases such as plasmin (1, 73–76). Plasmin is formed from its precursor, plasminogen, by two activators, tissue-type plasminogen activator (tPA) which is involved in thrombolysis, and urokinase-type plasminogen activator (uPA) which plays a central role in tissue remodelling, including cancer invasion. The activation of plasminogen is regulated by two specific plasminogen activator inhibitors (PAI-1 and PAI-2). Both uPA and PAI-1 are present in various types of cancer tissue, and it was recently found that high levels of uPA and PAI-1 in breast cancer tissue each is associated with poor prognosis.

Immunohistochemical and in situ hybridization studies have revealed that in breast and colon cancer tissue, PAI-1 is expressed predominantly in stromal cells.

According to the invention it is contemplated that the high PAI-1 content found in malignant tumours from patients with poor prognosis as described in detail later is involved in promotion of tumour growth, invasion and/or metastasis, most likely by protecting the stromal element of the tumour from degradation due to plasminogen activation formed in the microenvironment during invasion. This invention relates to the suppression of inhibitors of proteases and/or of other matrix-degrading enzymes, in particular to the suppression of plasminogen activator inhibitors such as PAI-1 in cancer tissue resulting in inhibition of growth and/or invasion and/or metastasis of tumour e.g. by allowing autodegradation of the tumour tissue, impairment of cancer cell migration and/or impairment of tumour angiogenesis.

GENERAL BACKGROUND

Urokinase-Type Plasminogen Activator

The biochemistry of uPA has been reviewed previously (1). It is a serine protease, which is synthesized as an approximately 50 kD glycosylated single polypeptide chain pro-enzyme, pro-uPA, that is virtually catalytically inactive. The human uPA gene is located on chromosome 10 and is transcribed into a 2.5 kb long mRNA. Pro-uPA is converted into active uPA, consisting of two polypeptide chains (A and B) held together by a disulphide bond, the A-chain arising from the amino-terminal part of pro-uPA, and the B-chain arising from the carboxy-terminal part. The A-chain consists of two structural domains, a growth factor domain with homology to EGF, and a kringle domain (2). The B-chain is homologous to the catalytic part of other serine proteases, such as trypsin, chymotrypsin, and plasmin. Two-chain uPA can, by the metalloproteinase matrilysin (or PUMP-1) (3), be converted into a 33 kD catalytic active form of uPA consisting of the B-chain and the carboxy-terminal part of the A-chain (low molecular weight uPA), and a 17 kD non-catalytic fragment consisting of the N-terminal part of the A-chain.

uPA cleaves a single peptide bond in plasminogen, converting it into plasmin, that degrades a broad spectrum of proteins, including fibronectin, fibrin, and laminin (for a review see ref.(1)). In addition, plasmin activates latent forms of some metalloproteases (4) and affects various growth factor systems, e.g. by activating latent TGF-β (5,6) and dissociating IGF-I from its binding protein (7) and bFGF from the surface of some cell types (8).

Many cytokines and hormones control the expression of uPA in a cell specific way (see reference (9)).

uPA is produced by many cultured cell types of neoplastic origin. It has been found that explants of tumour tissue released more uPA than the corresponding normal tissue. uPA has been identified in extracts from human lung, colon, endometrial, breast, prostate and renal carcinomas, human melanomas, murine mammary tumours, the murine Lewis lung tumour, and in ascites from human peritoneal carcinomatosis. An immunohistochemical study of invasively growing and metastasing Lewis lung carcinomas in mice consistently showed the presence of uPA, but also a pronounced heterogenecity in the content of uPA in different parts of the individual tumours. A high uPA content was found in areas with invasive growth and degradation of surrounding normal tissue, while other areas were devoid of detectable uPA. The uPA was located in the cytoplasm of the tumour cells and extracelluarly surrounding the tumour cells.

Degradation of the surrounding normal tissue is a central feature of invasiveness of malignant tumours. The constant finding of uPA in malignant tumours and the findings indicating that uPA plays a role in tissue degradation in normal physiological events have led to the assumption that uPA plays a similar role in cancer development. The hypothesis of uPA playing a role in tissue destruction involves the assumption that plasmin, together with other proteolytic enzymes, degrades the extracellular matrix. It is noteworthy in this context that most components of the extracellular matrix can be degraded by plasmin. These include laminin, fibronectin, proteoglycans, and possibly some types of collagen, but not all. In addition, plasmin can activate latent collagenases which in turn can degrade the other types of collagen (4).

Many research groups have proposed that invasive tumour cells secrete matrix-degrading proteinases and that one of the crucial cascades is the plasminogen activation system. Regulation of the proteolysis can take place at many levels including tumour cell-host cell interactions and protease inhibitors produced by the host or by the tumour cells themselves. Expression of matrix-degrading enzymes is not tumour cell specific. The actively invading tumour cells may merely respond to different regulatory signals compared to their non-invasive counterparts (10).

The assumption that the plasminogen activation system, through a breakdown of extracellular matrix proteins, plays a role in invasiveness and destruction of normal tissue during growth of malignant tumours is supported by a variety of findings. These include a close correlation between transformation of cells with oncogenic viruses and synthesis of uPA, the finding that uPA is involved in tissue destruction in many non-malignant conditions, and the immunohistochemical localization of uPA in invading areas of tumours (see (1) for review).

Further support for this hypothesis has come from studies with anti-catalytic antibodies to uPA in model systems for invasion and metastasis. Such antibodies were found to decrease metastasis to the lung from a human uPA producing tumour, HEp-3, transplanted onto the chorioallantoic membrane of chicken embryos (11,12), penetration of amniotic membranes by B16 melanoma cells (13), basement membrane invasion by several human and murine cell lines of neoplastic origin (14), and formation of lung metastasis after intravenous injection of B16 melanoma cells in mice (15). In some of these studies (13,14), a plasmin-catalyzed activation of procollagenases appeared to be a crucial part of the effect of plasminogen activation.

Urokinase-Thype Plasminogen Activator Receptor

A specific cell surface receptor for uPA (uPAR) was first detected by a saturable binding of uPA to monocytes and monocyte-like cells (16) and has since been found on many types of cultured cancer cells (17). Human uPAR is a single polypeptide-chain, highly glycosylated protein with a molecular weight of 55–60 kD (18). It is translated from a 1.4 kb mRNA (19), encoded by a single gene located on chromosome 19.

It consists of three homologous domains. The amino-terminal domain (domain 1) contains the ligand binding region (20), which binds to the EGF-like domain in the uPA molecule (21). uPAR is carboxy-terminally anchored to the cell surface by a glycosyl-phosphatidylinositol moiety (22). A possible function of this lipid anchor is to facilitate movement of uPAR on the cell membrane. uPAR can be cleaved by uPA and plasmin, releasing domain 1 and leaving domains 2 and 3 on the cell surface (23).

uPAR binds both active uPA and pro-uPA with a high affinity ($K_d$ $10^{-9}$–$10^{-11}$M), that depends on the cell type. Pro-uPA can be activated when it is receptor-bound, and receptor-bound uPA is catalytically active (17,24). Binding of pro-uPA to uPAR and concomitant cell surface binding of plasminogen strongly enhances plasmin generation (24,25) and the surface of uPAR expressing cells are preferential sites for plasminogen activation under physiological conditions (26).

The activation of receptor-bound pro-uPA is efficiently catalyzed by surface bound plasmin leading to a strong amplification of the overall plasminogen activation reaction (24). Several other proteolytic enzymes, including plasma kallikrein (27) and cathepsin B (28) can activate pro-uPA. The physiological relevance of these latter enzymes in pro-uPA activation remains to be determined and it is still not known how the uPA pathway of plasminogen activation is initiated in vivo.

uPAR synthesis is regulated by cytokines such as TGF-β1, TGF-β2, EGF and by the tumour promoter phorbol myristate acetate. This regulation has in some cases been traced back to the transcriptional level, but also changes in the stability of uPAR mRNA play a role ((29,30) and L. Lund, personal communication).

Type 1 and 2 Plasminogen Activator Inhibitor uPA activity is controlled by two specific plasminogen activator inhibitors, PAI-1 and PAI-2 (for a review see (31)). These molecules are products of different genes, located on chromosome 7 and 18, respectively. They are both glycoproteins with a molecular weight of approximately 50 kD and both belong to the serine protease inhibitor (serpin) family. PAI-1 and PAI-2 differ in their relative ability to react with uPA and tPA and also in their immunological reactivity. PAI-1 autoinactivates into a latent form but is protected from this inactivation by binding to vitronectin (32). uPA and tPA are also inhibited by protease-nexin 1, which in contrast to PAI-1 and PAI-2, also inhibits other trypsin-like proteases such as plasmin and thrombin (33). The inhibitors bind to the catalytic B-chain of active uPA. They do not react with pro-uPA. PAI-1 inhibits receptor-bound uPA nearly as efficiently as uPA in solution (24). Several cell types internalize and degrade complexes between uPA and PAI-1 or PAI-2 (34). In some cases this internalization appears to be dependent on binding to the uPA receptor (35) and recent reports indicate that the α-2-macroglobulin receptor in some cell types also plays a role in internalization of uPA/PAI-1 complexes (36). Expression of both PAI-1 and PAI-2 is regulated by a variety of cytokines, growth factors and hormones (31). The regulation of the various components of the uPA system appears to be independent of each other (9,29–31).

Localization of the Urokinase Plasminogen Activation System in Cancer Tissue

Studies of the occurrence and localization of the various components of the uPA system have shown that both uPA and uPAR are expressed at invasive foci in most experimental and human cancers that have so far been investigated. These studies have been performed both at the protein level by immunohistochemistry, and at the mRNA level by in situ hybridization. Because of the strong amplification of the proteolytic activity that is characteristic for the plasminogen activation cascade, uPA and uPAR are of very low abundancy in tissues.

In the highly invasive murine Lewis lung carcinoma, uPA protein (37) and mRNA (70) are consistently expressed by the cancer cells at invasive foci, and using a recently isolated cDNA for mouse uPAR (38) it has been found that also uPAR mRNA in this experimental carcinoma is expressed by the invading cancer cells (J.Eriksen, personal communication). PAI-1 protein is not found in the invasive areas of the Lewis lung carcinoma but is expressed by the cancer cells in non-invasive areas, suggesting that this inhibitor plays a role in protecting the tumour tissue against the proteolytic degradation (39).

An interesting finding is that Lewis lung carcinoma cells when migrating into the surrounding normal tissue without degrading it often express both uPA mRNA and PAI-1 mRNA (P. Kristensen, personal communication), suggesting that uPA activity regulated by PAI-1 is involved in migration of cancer cells. A role of uPA and PAI-1 in cell migration is also supported by a distinct localization of uPA found at cell-cell and focal cell substratum contacts in some cultured cell types. These cells also produce PAI-1 which may serve to regulate uPA activity, enabling it to act in a directional breaking up of such contacts during cell movement (72). An involvement of uPA and PAI-1 in cancer cell migration and metastasis is furthermore supported by the finding that out of 5 melanoma cell lines those 2 which produced both uPA, uPAR and PAI-1 were the most efficient in an in vitro matrix-degradation assay and most frequently produced lung metastasis in nude mice in vivo (71).

Of human cancers, colon adenocarcinomas have been most intensively studied for expression of components of the plasminogen activation system. Both uPA and uPAR are consistently present at invasive foci, but uPA protein (40) and mRNA (41) are not found in the cancer cells but in fibroblast-like stromal cells located adjacent to the invading cancer cells. uPAR mRNA (41) and protein (C. Pyke, unpublished results) are located in cancer cells and in tumour infiltrating macrophages. Therefore, in this type of cancer the malignant cells and the macrophages can presumably bind and utilize uPA released from the fibroblast-like cells. PAI-1 mRNA is in colon adenocarcinomas expressed by endothelial cells in the tumour stroma (42), while there is no PAI-1 expression in the surrounding normal tissue, suggesting that PAI-1 also in this type of cancer plays a role in protecting the tumour tissue against degradation. Another possible role of PAI-1 is to participate in the process of tumour angiogenesis (77).

In human squamous skin cancer both uPA and uPAR mRNA are expressed by the invading cancer cells (43,44). In ductal mammary carcinomas uPAR immunoreactivity is located in macrophages infiltrating the invasive foci (45), while uPA mRNA is found in adjacent fibroblast-like cells, and in some cases also in the cancer cells (43,46). PAI-1 has been detected by immunohistochemistry in endothelial cells, cancer cells and some non-malignant epithelial cells in breast cancer (47).

These studies thus show that there is a consistent expression of uPA and uPAR at invasive foci and of PAI-1 in non-invasive areas of malignant tumours as well as in endothelial cells lining the tumour vessels, and that some of the components of the uPA system are expressed by the stromal cells during cancer invasion.

A similar stromal cell expression has recently been found for several metalloproteases believed to be involved in cancer invasion (48–52) and a picture is now emerging of the stromal cells often being actively involved in the invasive process (for a recent review see (53)).

Prognostic Significance of uPA and PAI-1 in Breast Cancer

The first study which related uPA content in breast cancer tissue to patient prognosis (54) measured uPA levels by assaying the enzyme activity present in the tumour extracts and demonstrated that high activity was significantly associated with shorter disease-free interval. Subsequent studies measuring the uPA content by ELISA showed that high levels of uPA immunoreactivity was not only associated with shorter relapse-free survival but also strongly associated with short overall survival (55–58).

Jänicke et al., (56) thus found in a study of 115 patients with a medium observation time of 12.5 months, that patients with high uPA levels had significantly shorter disease-free survival, the relative risk being 21.1 (95% confidence interval 2.6–174.6). This association was significant in both node-negative and node-positive patients. Similarly, Duffy et al (55) found a significant correlation between survival and uPA-level in 166 breast cancer patients with a medium observation time of 34 months, the relative risk being 11.3 (95% confidence interval 1.22–99.0).

These two studies were performed with detergent extracts of mammary cancer tissue. These extracts contain more uPA than those performed with detergent-free buffers, such as those used for routine preparation of cytosols for steroid hormone receptors (59). By the use of a combination of one polyclonal antibody preparation and three monoclonal antibodies an ELISA was constructed that readily detects uPA immunoreactivity in cytosols. Although the cytosols only contain about 12% of the optimally extractable uPA immunoreactivity, there is a close correlation between the uPA in the cytosols and the maximally extractable amount (59). With this uPA ELISA a retrospective study was performed on stored cytosols from 190 pre- and postmenopausal high risk patients who were protocolled by the Danish Breast Cancer Cooperative Group and had a medium observation time of 8.5 years (58). High cytosolic uPA was in this study significantly associated with short overall survival in both pre- and postmenopausal patients, the relative risk being 2.0 (95% confidence intervals 1.1–3.7) in the premenopausal women.

In a recent study by Foekens et al (60) uPA was assessed in breast cancer cytosol from 671 women. uPA was found significantly associated with relapse-free survival and death both in the group of node negative patients and in the group of node positive patients.

Also high PAI-1 level in mammary cancer tissue, as determined by ELISA, appears to be associated with poor prognosis (57,58). Janicke et al. (57) thus found in a study of 113 patients with a medium observation time of 25 months that patients with high PAI-1-level in their primary tumour had a significantly shorter relapse-free survival than patients with low PAI-1-level, the relative risk being 2.8 (95% confidence interval 0.98–8.3). In the Danish study of 190 high risk breast cancer patients (58), high PAI-1 level in cytosolic extracts was significantly correlated to short overall survival and short relapse-free survival in both pre- and postmenopausal patients, the relative risk with respect to overall survival being 2.9 (95% confidence interval 1.5–5.8) in postmenopausal women.

There is a positive correlation between uPA and PAI-1 levels in breast cancer tissue (47,57,58) while the two parameters in the various studies are not, or only weakly associated with, estrogen and progesterone receptor level. In multivariate analyses including established prognostic parameters, such as number of tumour positive lymph nodes, tumour size, and estrogen and progesterone receptor levels, levels of either uPA or PAI-1 are found to be independent and statistically significant prognostic parameters in most patient groups studied (55,57,58). Determination of uPA- and PAI-1 levels thus appears to add significant prognostic information to that obtained by the established parameters. It should be noted that this information, at least regarding PAI-1 levels, can be obtained from cytosols routinely prepared for steroid hormone receptor analysis.

SUMMARY OF THE INVENTION

The fact that high PAI-1 level in the tumour tissue is correlated to poor prognosis in breast cancer and also in lung adenocarcinoma (see Example 1) suggests that PAI-1 promotes tumour growth, invasion and/or metastasis. As discussed above there are several mechanisms by which PAI-1 may play such a promoting role such as protecting the tumour tissue against degradation by the uPA system, participating in cancer cell migration, participating in tumour angiogenesis, or interfering with activation/inactivation of growth factors. It is likely that some inhibitors of other extracellular proteolytic enzymes and other non-proteolytic matrix-degradating enzymes play a similar role in promoting tumour growth, invasion and/or metastasis.

Thus, the invention relates to a method of inhibiting malignant tumour growth, invasion and/or metastasis in a patient who has been established to have a high risk of developing a malignant tumour or who has developed a malignant tumour, the method comprising suppressing the inhibitory activity of an inhibitor of a protease or of a non-proteolytic matrix-degrading enzyme in malignant tumour tissue or potential malignant tumour tissue.

DETAILED DESCRIPTION OF THE PREFERRED EMBODIMENTS OF THE INVENTION

Figure 1:
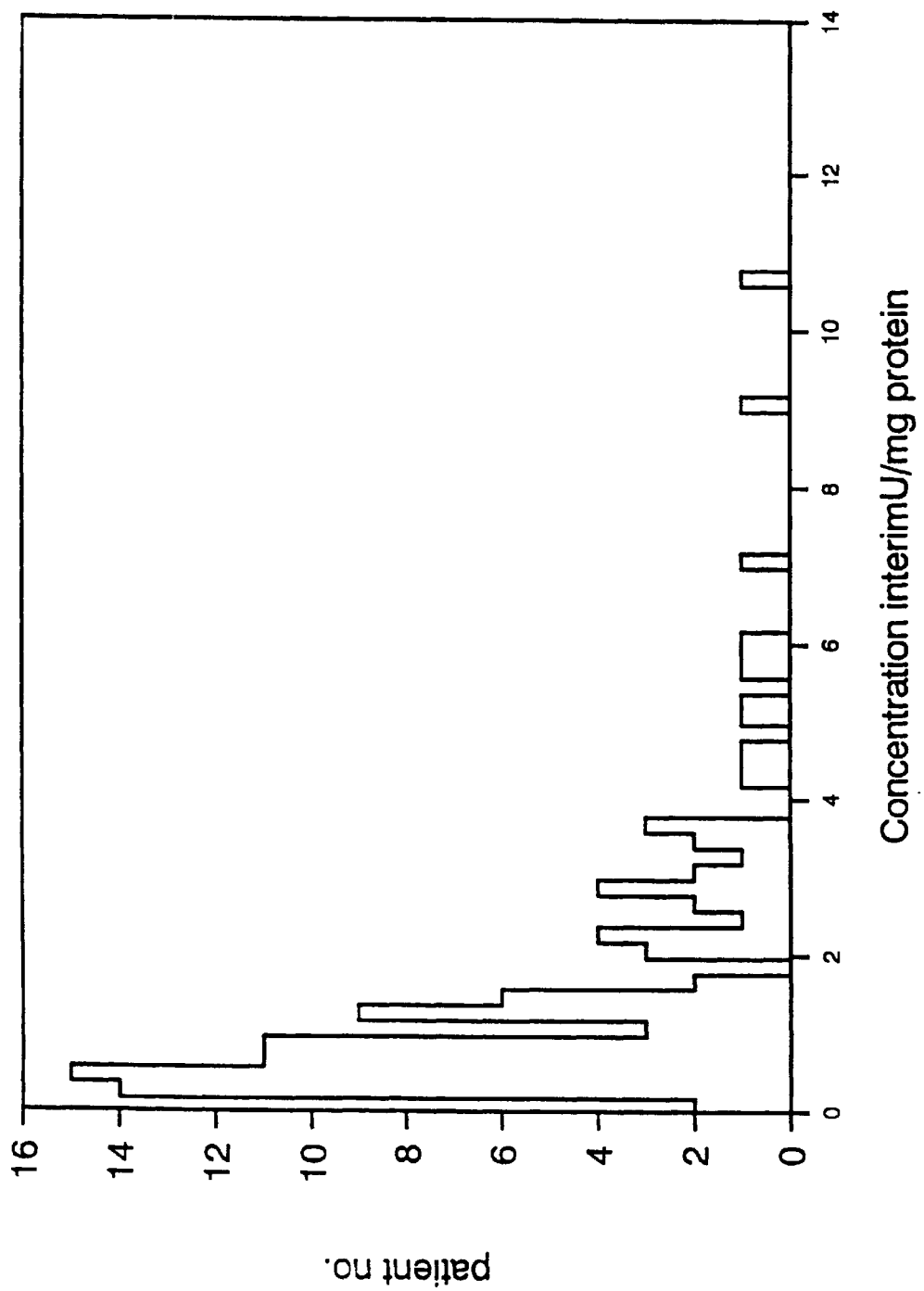
FIG. 1. Shows the distribution of PAI-1 in tumor extracts (Example 1).

By the method of the invention the inhibitory effect of the said inhibitor in the malignant tumour tissue or potential malignant tumour tissue is suppressed, inhibited or neutralized, thereby allowing degradation of the malignant tumour tissue or the potential malignant tumour tissue. By the term "suppression" is meant that the inhibitory activity of an inhibitor of a protease or of a non-proteolytic matrix-degrading enzyme is significantly reduced i.e. by a degree of at least 25% but preferably reduced by a higher degree such as about 50%, 60%, 70% or even more such as 75%, 80%, 90% or 95%. The degree of inhibition of the inhibitor in question by various compounds can be established by use of suitable inhibitory tests. In the present context, the term "compound" should be understood as in its broadest context as a substance composed of two or more elements, such that the atoms of the elements are firmly linked together and are present in definite proportions, the term thus including conventional chemical compounds as well as e.g. antibodies. Examples of such tests which may be used separately or successively are described in Examples 4, 5 and 6 using the inhibitor PAI-1 as an example. Evidently it will be within the skill of the man skilled in the art based upon the teaching in the specification to develop and use other similar tests for the purpose of screening compounds being capable of suppressing the inhibitory activity of an inhibitor of a protease or of a non-proteolytic matrix-degrading enzyme.

The above degree of suppression thus relate to in vitro tests, whereas the suppression is to take place in malignant tumour tissue or potential malignant tumour tissue. It will thus be necessary to test the compounds which have been found inhibitory in in vitro tests and/or in vivo animal test systems also in clinical trials in order to establish whether a certain compound will be suitable for use in the methods according to the invention, the planning and conduct of such clinical trials being within the skill of the man skilled in the art.

By the term "a patient who has been established to have a high risk of developing a malignant tumour or who has developed a malignant tumour" is meant a human being (or an animal) who by use of any means of investigation or test known within the art of medicine and surgery has been established to have developed a malignant tumour. By the term "to have a high risk of developing a malignant tumour" is intended to include the situation in which it is not definitively established that the human or animal has developed a malignant tumour but it is contemplated highly likely that he or she has in fact done so or will do so in the near future, i.e. within the coming days, months or years. A such situation will arise e.g. after surgery for a malignant tumour in which situation is can not generally be excluded that metastasis has already taken place as well as in certain clinical situations in which one or a number of clinical or laboratory tests indicate that the patient has developed a malignant tumour but the localization of the tumour is not established and also situations where the patient has a high-risk-indicating score of a tumour marker such as a serum tumour marker or a gene or gene product which indicates that the patient is at high risk of developing a malignant tumour. Examples of such tumour markers are well-known within the art.

The term "malignant tumour" or "malignant tumour tissue" is intended to designate the malignant tumour cells themselves, including micrometastases, as well as the extracellular matrix and the stromal cells of the malignant tumour, e.g. endothelial cells, fibroblasts, macrophages, leucocytes etc.

The term "potential malignant tumour tissue" is intended to designate tissue that has the potential to develop into a malignant tumour.

The term "matrix-degrading enzyme" as used herein, denotes an enzyme which is capable of degrading components of the extracellular matrix, i.a. proteins. Important matrix-degrading enzymes are proteases and an important aspect of the invention is thus the above-mentioned method wherein the protease inhibitory activity of a protease inhibitor is suppressed. However, also non-proteolytic enzymes play a role in matrix-degradation, e.g enzymes degrading the extracellular proteoglycanes.

According to the invention such suppression of the inhibitory activity of an inhibitor of a protease or of a non-proteolytic matrix-degrading enzyme in malignant tumour tissue or potential malignant tumour tissue allows the protease or the non-proteolytic matrix-degrading enzyme directly or indirectly to degrade the malignant tumour tissue or the potential malignant tumour tissue, and/or results in interference with the process of tumour angiogenesis, and/or results in interference with the migrating capacity of malignant tumour cells or of other cells in the tumour stroma and/or results in interference with the effect of growth factors.

By the term "migrating capacity" as used herein is meant the capability of tumour cells to invade non-malignant tissue. Thus, the term relates to both the invasiveness of tumour cells as well as their capability of forming metastases. An interference with the migrating capacity will thus result in a reduction of invasiveness as well as the capability of forming metastatic tissue.

The patient may be treated solely by the method of the invention. In a number of cases, however, the patient will be subjected also to other forms of treatment, e.g. an operation at which the malignant tumour tissue is removed. In such cases, the treatment according to the invention may be performed as a neoadjuvant treatment, as preoperative treatment, as adjuvant treatment or as any kind of combination of these treatments. Also combinations with cytotoxic drugs, endocrine therapy and irradiation represent possible treatment strategies.

In certain circumstances it has not yet been established that a person has developed a malignant tumour, but it is considered highly likely that he or she is in the process of developing a malignant tumour or has developed a malignant tumour but the localization of the tumour has not yet been established. Within the scope of the present invention is also a method of treatment wherein the patient is a patient who has been established to have a high risk of developing a malignant tumour e.g. by having a high-risk-indicating score of a tumour marker such as a serum tumour marker or by having a gene or gene product which indicates that the patient is at high risk of developing a malignant tumour.

For a number of malignant tumour types, e.g. mammary cancer, as described above, an increased concentration of the inhibitor of the protease or the non-proteolytic matrix-degrading enzyme has been established to be a prognostic factor indicating a poor prognosis for the patient having the type of malignant tumour in question. The "increased concentration" can thus be above an established "normal value" for e.g. a plasma sample or tissue sample from a particular tissue, or for a certain tumour the concentration can be high when the values of different tumours of the same type are compared (see as an example Example 1).

A very important embodiment of the present invention thus relates to a method of treatment according to the invention wherein the patient is a patient who has an increased concentration of the inhibitor of the protease or the non-proteolytic matrix-degrading enzyme in the tumour tissue and/or in plasma and/or serum. The increased concentration of the inhibitor of the protease or the non-proteolytic matrix-degrading enzyme in the malignant tumour tissue and/or in plasma is established preoperatively or postoperatively or it might be established on the basis of a plasma sample (with or without operation) or a sample from the malignant tumour, e.g. a biopsy.

This embodiment is relevant wherein the patient has a malignant tumour type for which it has already been established that an increased concentration of the inhibitor of the protease or the non-proteolytic matrix-degrading enzyme in the malignant tumour tissue and/or in plasma is associated with a poor prognosis. For a number of malignant tumour types it is not yet known if an increased concentration of the inhibitor of the protease or the non-proteolytic matrix-degrading enzyme is a prognostic factor indicating a poor prognosis for the type of malignant tumour in question. Within the scope of the present invention is also a method for establishing, for a malignant tumour type, the prognostic score of an increased concentration of malignant tumour tissue inhibitor of protease or non-proteolytic matrix-degrading enzyme and/or an increased concentration of plasma inhibitor of the protease or the non-proteolytic matrix-degrading enzyme by using an assay specific for the inhibitor of the protease or the non-proteolytic matrix-degrading enzyme. An example of the establishment of such a prognostic score for a certain cancer type is given in Example 1 with reference to lung cancer by use of an PAI-1 ELISA.

The present invention thus also relates to a method for establishing the predictive value for having benefit from being treated with a compound which suppresses the inhibitory activity of an inhibitor of a protease or of a non-proteolytic matrix-degrading enzyme in malignant tumour tissue or potential malignant tumour tissue in an individual patient, i.e. to predict the probability of a response of a treatment with the compound in an individual patient. Examples of malignant tumour types for which this has been established or will be established are mammary carcinomas, urological carcinomas e.g. prostate carcinoma and bladder carcinoma, gynaecological carcinomas e.g. ovarian carcinoma and cervical carcinoma, non-small cell lung tumours, gastrointestinal cancers e.g. colon adenocarcinoma and gastric cancers, brain tumours, sarcomas, haematological malignancy e.g. lymphoma and skin cancers e.g. melanoma and squamous cell skin cancer. Also any other cancer type such as e.g. head and neck cancer for which it is established that an increased concentration of the inhibitor of the protease or of the non-proteolytic matrix-degrading enzyme is a prognostic factor or has a predictive value are within the scope of the invention.

Within the scope of the invention is thus also a method of treatment according to the invention, wherein the increased concentration of the inhibitor of the protease or the non-proteolytic matrix-degrading enzyme has been established to be a predictive factor indicating efficiency of the treatment on the type of malignant tumour in question with the suppressor of the inhibitor of the protease or of the non-proteolytic matrix-degrading enzyme. An example of a predictive assay to identify patients who potentially will benefit from such a treatment is described in Example 2 using bronchogenic adenocarcinoma as an example. Similar experiments can be made for other tumour types.

As can be seen from example 2, it is contemplated that the efficacy of the treatment of patients suffering from malignant neoplasia by a method of the invention comprising inhibiting a protease inhibitor, can be evaluated a priori by determining the level of the protease inhibitor in the neoplastic tissue or in other samples taken from the patients (plasma, serum, urine etc.). Thus, by determining the level of e.g. PAI-1 in tumour tissue from a patient, it will be possible to establish whether there is any medical justification for the initiation of PAI-1 inhibition treatment in the patient.

Therefore, the invention also relates to a method for predicting the therapeutical efficacy of a therapeutical method of the invention, the method comprising
1) determining the level of PAI-1 in malignant or potentially malignant tissue or other samples (e.g. plasma, serum, urine etc.) from a subject which potentially is to be subjected to a therapeutical method according the invention, and
2) establishing that the said therapeutical efficacy is high if the PAI-1 level is beyond or equal to a predetermined threshold value, and that the said therapeutical efficacy is low if the PAI-1 level is below the pre-determined threshold value.

It will be understood, that this method of the invention for predicting therapeutic efficacy will be applicable also when the protease inhibitor is not PAI-1, as long as the determination of the inhibitor in the samples mentioned above is possible by the methods known by the person skilled in the art (immunoassays such as RIA and ELISA, assays depending on the determination of the biological activity of the protease inhibitor etc.). Therefore, the above-mentioned method for predicting therapeutical efficacy also relates to the determination of the level of other protease inhibitors which promote tumour growth, migration and metastasis.

The method according to the invention provides a method, wherein the malignant tumour tissue as defined above is degraded while substantially no other tissue than malignant tumour tissue is degraded to an extent or degree which give unacceptable side effects.

The inhibitor of the protease or of the non-proteolytic matrix-degrading enzyme is secreted from the malignant tumour cells themselves, including micrometastases, and/or from the stromal components of the malignant tumour, e.g. endothelial cells, fibroblasts, macrophages, leucocytes etc.

In one embodiment of the invention the inhibitor of the protease or the non-proteolytic matrix-degrading enzyme is a serine protease inhibitor, in another embodiment of the invention the inhibitor of the protease or of the non-proteolytic matrix-degrading enzyme is an inhibitor of a metalloprotease such as TIMP-1 or TIMP-2, in a third embodiment of the invention the inhibitor of the protease or of the non-proteolytic matrix-degrading enzyme is an inhibitor of a cysteine protease (thiol protease), in a fourth embodiment of the invention the inhibitor of the protease or of the non-proteolytic matrix-degrading enzyme is an inhibitor of an aspartic protease, in a fifth embodiment the inhibitor of the protease or of the non-proteolytic matrix-degrading enzyme is an inhibitor of any other protein degrading enzyme, in a sixth embodiment the inhibitor of the protease or of the non-proteolytic matrix-degrading enzyme is an inhibitor of a heperanase and in a seventh embodiment the inhibitor is an inhibitor of any other enzyme participating in degradation of the extracellular matrix.

An important aspect of the invention relates to methods according to the invention wherein the serine protease inhibitor is selected from the group consisting of plasminogen activator inhibitor type 1 (PAI-1), plasminogen activator inhibitor type 2 (PAI-2) and protease nexin 1.

The invention relates to various methods wherein the suppression of the inhibitory activity of the inhibitor of the protease or of the non-proteolytic matrix-degrading enzyme is obtained by administering to the patient a compound which suppresses the inhibitory activity of the inhibitor of the protease or of the non-proteolytic matrix-degrading enzyme. In particular, the invention relates to various methods according to the invention wherein the serine protease is PAI-1, such as a method, wherein the activity of PAI-1 in the tumour tissue is inhibited by administering to the patient a compound which suppresses the plasminogen activator-inhibitory activity of PAI-1.

As can be seen from example 6, one such compound has been identified, namely the antibody PAI-1 clone 2 (WO 87/00549). In narrow embodiments of the invention this antibody, active fragments thereof, and/or immunological equivalents thereof is the compound administered to the patient. The invention also relates to the use of this antibody in the treatment of neoplastic malignancies.

The antibodies can be used as whole antibodies, fragments thereof (e.g. FV, (FV)$_2$,Fab, Fab', F(ab)$_2$), chimeric, humanized or human antibodies as long as they are binding PAI-1 in a suitable manner. Short-chain antibody fragments containing only the CDR regions or parts thereof conferring the specific binding to PAI-1 are also suitable, especially if the antibody is a labelled one.

The term "active fragment" in this context denotes a binding fragment of the molecule, which is also capable of eliciting the same biological effects on the target molecule as is the antibody itself, although in some instances at higher concentrations than the antibody. By the term "immunological equivalent" is meant a substance exhibiting substantially the same binding specificity as the antibody, and exerting substantially the same effects on the target molecule as the antibody, although in some instances at higher concentrations than the antibody proper.

For prevention of an immune response, it is preferred to use antibodies/compounds which resemble as closely as possible antibodies of human origin. Such antibodies are, for example, chimeric or humanized (CDR-grafted) antibodies. Such antibodies usually are manufactured from a rodent monoclonal antibody (see e.g. for review: Morrison (1992), Annu. Rev. Immunol. 10, 239–265; Winter and Milstein (1991), Nature 349, 293–299). In a specifically preferred embodiment of the invention, tumour specific human antibodies (Borrebaeck et al. (1988), Proc. Natl. Acad. Sci. USA 85, 3995–3999; Borrebaeck (1988), Immunol. Today 9, 355–359) are used for therapeutic purposes. In addition, it is specifically preferred to prepare human Mabs via phage display libraries, as is described, for example, by Griffith et al., EMBO J. 12 (1993) 725–734.

Also the porcine antibodies disclosed in U.S. Pat. No. 4,132,768 have proven to be non-immunogenic or only very weakly immunogenic in human beings.

The compounds used for therapy in this invention may be administered parenterally, such as intravascularly, intraperitoneally, subcutaneously, intramuscularly, using forms known in the pharmaceutical art. The active drug components of the present invention are used in liquid, powdered or lyophilized form and may be combined with a suitable diluent or carrier, such as water, a saline, aqueous dextrose, aqueous buffer, and the like. Preservatives may also be added.

Regardless of the route of administration selected, the compounds used in the present invention are formulated into pharmaceutically acceptable dosage forms by conventional methods known to those skilled in the art. The compounds may also be formulated using pharmacologically acceptable acid or base addition salts. Moreover, the compounds or their salts may be used in a suitable hydrated form.

Regardless of the route of administration selected, a non-toxic but therapeutically effective quantity of one or more compounds used in this invention is employed in any treatment. The dosage regimen for treating is selected in accordance with a variety of factors including the type, age, weight, sex and medical condition of the patient, type of tumour, the route of administration, and the particular compound employed in the treatment. A physician of ordinary skill can readily determine and prescribe the effective amount of the drug required regarding known antibody therapy approaches. In so proceeding, the physician could employ relatively low doses at first, and subsequently, increased dose until a maximum response is obtained.

The above-described method also comprises one, wherein the compound is a compound which suppresses the plasminogen activator-inhibitory activity of PAI-1 by inhibiting the binding of PAI-1 to vitronectin and a method, wherein the compound is a compound which inhibits the binding of PAI-1 to uPA, but does not inhibit the binding of uPA to uPAR. An example of a suitable compound is a compound which is capable of binding to PAI-1 but not capable of converting plasminogen into plasmin, e.g. a non-catalytic variant, derivative or analogue of uPA. Another example of a suitable compound is an antibody which is capable of binding to PAI-1 and thereby inhibiting the inactivation of uPA. A third example is a compound binding to the protease, e.g. uPA, preventing the effect of the inhibitor, but not inhibiting the protease. Such a compound may be an antibody against the protease. In still another embodiment of the invention the compound which is capable of binding to a protease inhibitor, may have a cytotoxic agent coupled to the compound.

Apart from a method of the invention, wherein a compound is administered and directly inhibits the effects exerted by the inhibitor, another scheme is possible. As disclosed in WO 91/01379 it is possible to transscriptionally modulate the expression of homologous genes by contacting cells expressing the gene. WO 91/01379 is incorporated herein by reference.

By employing this technique, the expression of e.g. PAI-1 could be impaired by i.a. targeting molecules to the DNA fragment encoding PAI-1 and thereby inhibiting the expression of PAI-1.

The malignancy of a tumour might not in itself be due to the tumour cells producing uPA or PAI-1. Other cells present in the tumour may supply the malignant cells with uPA or PAI-1 whereby the tumour is protected from autodegradation.

Another important embodiment of the invention therefore comprises a method wherein malignant cells of the malignant tumour produce uPA, the PAI-1 being produced by other cells in the malignant tumour or, conversely, a method, wherein malignant cells of the malignant tumour produce PAI-1, the uPA being supplied by other cells in the malignant tumour. Finally, also a part of the invention is a method, wherein malignant cells of the malignant tumour produce neither uPA nor PAI-1, the uPA and the PAI-1 being supplied by other cells in the malignant tumour.

In a recent in situ hybridization study PAI-1 mRNA was found to be located in endothelial cells in the tumour stroma of invasive ductal breast carcinomas (C. Pyke, unpublished results). Subsequent immunohistochemistry confirmed the localization of PAI-1 to the tumour vessels (C. Pyke, unpublished results).

The association between high PAI-1 level and poor prognosis in breast cancer may be related to the above described findings of PAI-1 mRNA being expressed by cells in the tumour stroma and not by cells in the surrounding normal tissue, suggesting a function of PAI-1 in protecting the tumour tissue against the proteolytic degradation which the tumour imposes upon the surrounding normal tissue. Thus, inhibition of PAI-1 may lead to degradation of the tumour stroma including tumour vessels and thereby inhibition of tumour progression.

In Example 3 is described in situ hybridization for PAI-1 mRNA and immunostaining of PAI-1 protein in human lung cancer. For other cancer types for which it is established that an increased concentration of PAI-1 is a prognostic factor, similar experiments may be performed.

In order to neutralize inhibitors of the protease or the non-proteolytic matrix-degrading enzyme in the tumour tissue it would be desirable to apply a local therapy, thereby reducing potential side effects on normal tissue.

One aspect of the invention is thus to suppress the activity of the inhibitor of the protease or of the non-proteolytic matrix-degrading enzyme by administering, locally or systemically, to the patient, stromal cells which have been transformed with a genetic construct expressing a gene product suppressing the inhibitor of the protease or of the non-proteolytic matrix-degrading enzyme. One possibility would be to use genetically engineered tumour infiltrating fibroblasts (PCT/DK92/00306), published as WO 93/08301.

In an important embodiment of the invention the stromal cells are capable of finding and infiltrating a malignant tumour of a mammal genotype, in particular human genotype, in an immunodeficient non-human recipient vertebrate into which malignant tumour cells of the said mammal genotype have been introduced, the stromal cells containing 1) a gene which, when it is expressed in the immunodeficient recipient vertebrate by stromal cells which are capable of finding and colonizing, in the recipient vertebrate, colonies of malignant tumour cells of the said mammal genotype, is capable of controlling the progression of the malignant tumour cells of the said mammal, and
2) a promoter securing expression of the gene product when the stromal cells have been transferred to the said mammal.

The invention also relates to methods, wherein the stromal cells are tumour-infiltrating stromal cells which are capable of finding malignant tumour cells in the patient, and it is preferred that the stromal cells are of a tissue type which is compatible with the tissue of the patient. An especially preferred method of the invention is a method wherein the stromal cells are stromal cells from the patient himself.

An important embodiment of the invention relates to a screening method for selecting compounds which are suitable for suppressing the inhibitory activity of an inhibitor of a certain protease or non-proteolytic matrix-degrading enzyme e.g. PAI-1 against uPA, the method comprising one or more of the following steps:
1) A screening assay in which the possible suppression of the inhibitory activity of an inhibitor of a protease or of a non-proteolytic matrix-degrading enzyme is determined by adding the compound to a system comprising immobilized inhibitor of the protease or of the non-proteolytic matrix-degrading enzyme and solubilized protease or non-proteolytic matrix-degrading enzyme, the protease or the non-proteolytic matrix-degrading enzyme bound to the inhibitor of the protease or of the non-proteolytic matrix-degrading enzyme being detected by the enzyme being labelled or by means of a labelled antibody directed to the protease or the non-proteolytic matrix-degrading enzyme, or adding the compound to a system comprising immobilized protease or non-proteolytic matrix-degrading enzyme and solubilized inhibitor of the protease or of the non-proteolytic matrix-degrading enzyme, inhibitor of the protease or of the non-proteolytic matrix-degrading enzyme bound to the protease or the non-proteolytic matrix-degrading enzyme being detected by the inhibitor being labelled or by means of a labelled antibody directed to the inhibitor of the protease or of the non-proteolytic matrix-degrading enzyme.
2) An assay in which the possible suppression of the inhibitory activity of the inhibitor of the protease or of the non-proteolytic matrix-degrading enzyme in the tumour tissue is determined by adding the compound to a system comprising radiolabelled inhibitor of the protease or of the non-proteolytic matrix-degrading enzyme and tumour cells expressing the protease or the non-proteolytic matrix-degrading enzyme and detecting any inhibitor of the protease or of the non-proteolytic matrix-degrading enzyme binding to the protease or the non-proteolytic matrix-degrading enzyme by gamma counting of the cells.
3) A screening assay, in which the potential suppression of the inhibitory activity of an inhibitor of a protease or of a non-proteolytic matrix-degrading enzyme by the compound is determined by using whole cells to which the protease or the non-proteolytic matrix-degrading enzyme is bound on the surface, e.g. by a protease receptor, such as uPA to the uPA receptor.

The assay is based on the principle described for determining the inhibition of receptor bound uPA by plasminogen activator inhibitors (61). This assay is based on the inhibition of plasmin generation using the plasmin-specific fluorogenic substrate H-D-Val-Leu-Lys-7-amido-4-methylcoumarin (Bachem). The inhibitory effect of the test compound against PAI-1 is then determined by comparison of the plasmin generation curves obtained with the various concentrations of the compound with plasmin generation curves made with varying concentrations of PAI-1.
4) Administering a compound which has been established to suppress the inhibitory activity of an inhibitor of a protease or of a non-proteolytic matrix-degrading enzyme in the tumour tissue to a nude mouse or a nude rat which is inoculated with human malignant tumour cells which are capable of invasion and/or metastasis in the mouse or rat in the presence of the protease or the non-proteolytic matrix-degrading enzyme and the inhibitor of the protease or of the non-proteolytic matrix-degrading enzyme, and selecting, as a suitable compound, a compound inhibiting the growth and/or invasion and/or metastasis of the human malignant tumour cells in the mouse or the rat.

The tumour cells included in this assay can either be producing protease or non-proteolytic matrix-degrading enzyme but not producing the inhibitor of the protease or the non-proteolytic matrix-degrading enzyme, the inhibitor being supplied by either mouse cells or by other human cells with which the mouse is inoculated; tumour cells producing the inhibitor of the protease or the non-proteolytic matrix-degrading enzyme, the protease or the non-proteolytic matrix-degrading enzyme being supplied by mouse cells or by human cells with which the mouse is inoculated; tumour cells producing both the protease or the non-proteolytic matrix-degrading enzyme and the inhibitor of the protease or the non-proteolytic matrix-degrading enzyme or tumour cells producing non of these components, the protease or the non-proteolytic matrix-degrading enzyme and its inhibitor being supplied by mouse cells or by inoculated human cells.

An important embodiment of the invention relates to a method as described above, wherein the protease inhibitor is PAI-1.

It will be understood that compounds selected by the above-described methods are valuable compounds in the method of the invention for inhibiting malignant tumour growth, migration etc. as well as in the uses according to the invention. Such compound can also be used for the preparation of pharmaceutical compositions as discussed below.

Alternatively, in order to generate inhibitors of PAI-1, activity affinity screening of large, highly diverse libraries of peptides expressed on the surface of filamentous bacteriophage particles can also be performed. This recently developed powerful technique (81–84) is based on the ability of filamentous phages to display foreign peptides on their outer surfaces and involves the specific screening and affinity purification of bacteriophages displaying peptides that are ligands for a particular protein (85). Filamentous bacteriophage libraries have successfully been used to identify peptides binding to diverse molecules such as streptavidin (86), HLA class II protein (87), and even a lectin (88).

The phage display vector systems pComb3 (89) and pComb8 (90), originally developed for the expression of Fab fragments, but also successfully used for expression of PAI-1 (91) as well as for a $\alpha_2$MR/LRP random fragment library (92), results in monovalent display and multivalent display, respectively. Hence, construction of peptide libraries in both of the phage display vectors pComb3 and pComb8 will allow for isolation of bacteriophages containing peptides of high- and low affinity binding of PAI-1, respectively.

In short, the following steps can be used:

Immobilization of PAI-1 in Costar microtiter wells. Incubation ("panning") with above mentioned phage libraries. After washing bound phages are eluted using glycine-HCl (pH 2.2) and neutralized. Eluted phages are then reamplified. The panning, washing, elution and amplification protocol is repeated 3 times in total. DNA from phages isolated after the final round of panning are isolated and DNA "peptide-inserts" of the corresponding phages are sequenced according to standard DNA sequencing procedures. Synthetic peptides can then be produced and tested for their ability to inhibit the PAI-1/uPA interaction in an in vitro assay (see later). Peptide consensus motives identified as inhibitors of PAI-1 function will be extended on each side for construction of new phage display peptide libraries and the whole outlined procedure will be repeated for isolation of new peptides with higher binding affinities for PAI-1 (93).

The tumour cells included in the above mentioned assay can either be uPA producing but not PAI-1 producing, the PAI-1 being supplied by mouse cells or by human cells with which the mouse is inoculated; PAI-1 producing tumour cells, the uPA being supplied by mouse cells or by human cells with which the mouse is inoculated; tumour cells producing both the uPA and the PAI-1 or the tumour cells producing neither uPA nor PAI-1, uPA and PAI-1 being supplied by mouse cells or other inoculated human cells.

An important embodiment of the invention relates to a compound which is a suppressor of an inhibitor of a protease or of a non-proteolytic matrix-degrading enzyme in malignant tumour tissue or potential malignant tumour tissue for use as a medicament, i.e. for use for inhibiting malignant tumour growth, invasion and/or metastasis in a patient who has been established to have a high risk of developing a malignant tumour or who has developed a malignant tumour, such as a compound, which allows the protease or the non-proteolytic matrix-degrading enzyme directly or indirectly to degrade the malignant tumour tissue or the potential malignant tumour tissue by the suppression of the inhibitory activity of an inhibitor of a protease or of a non-proteolytic matrix-degrading enzyme in malignant tumour tissue or potential malignant tumour tissue.

In particular, the invention relates to a compound which
1) suppresses the inhibitory activity of an inhibitor of a protease or of a non-proteolytic matrix-degrading enzyme as determined by adding the compound to a system comprising immobilized inhibitor of the protease or of the non-proteolytic matrix-degrading enzyme and solubilized protease or non-proteolytic matrix-degrading enzyme, the protease or the non-proteolytic matrix-degrading enzyme bound to the inhibitor of the protease or of the non-proteolytic matrix-degrading enzyme being detected by the enzyme being labelled or by means of a labelled antibody directed to the protease or the non-proteolytic matrix-degrading enzyme, or by adding the compound to a system comprising immobilized protease or non-proteolytic matrix-degrading enzyme and solubilized inhibitor of the protease or of the non-proteolytic matrix-degrading enzyme, inhibitor of the protease or of the non-proteolytic matrix-degrading enzyme bound to the protease or the non-proteolytic matrix-degrading enzyme being detected by the inhibitor being labelled or by means of a labelled antibody directed to the inhibitor of the protease or of the non-proteolytic matrix-degrading enzyme, and/or
2) suppresses the inhibitory activity of the inhibitor of the protease or of the non-proteolytic matrix-degrading enzyme in the tumour tissue as determined by adding the compound to a system comprising radiolabelled inhibitor of the protease or of the non-proteolytic matrix-degrading enzyme and tumour cells expressing the protease or the non-proteolytic matrix-degrading enzyme and detecting any inhibitor of the protease or of the non-proteolytic matrix-degrading enzyme binding to the protease or the non-proteolytic matrix-degrading enzyme by gamma counting of the cells, and/or
3) suppresses the inhibitory activity of an inhibitor of a protease or of a non-proteolytic matrix-degrading enzyme as determined by using whole cells to which the protease or the non-proteolytic matrix-degrading enzyme is bound on the surface, e.g. by a protease receptor, such as uPA to the uPA receptor, and/or
4) inhibits the growth and/or invasion and/or metastasis of human malignant tumour cells in a nude mouse or a nude rat as determined by administering to the nude mouse or the nude rat, which has been inoculated with human malignant tumour cells which are known to invade and/or metastasize in the presence of the protease or the non-proteolytic matrix-degrading enzyme and the inhibitor of the protease or of the non-proteolytic matrix-degrading enzyme and which are capable of invasion and/or metastasis in the mouse, the compound which has been established to suppress the inhibitory activity of an inhibitor of a protease or of a non-proteolytic matrix-degrading enzyme in the tumour tissue.

In another aspect, the invention relates to the use of a compound, which suppresses the inhibitory activity of an inhibitor of a protease or of a non-proteolytic matrix-degrading enzyme in malignant tumour tissue or potential malignant tumour tissue, for preparing a composition for inhibiting malignant tumour growth, invasion and/or metastasis in a patient who has been established to have a high risk of developing a malignant tumour or who has developed a malignant tumour.

In particular, the invention relates to the use as described above, wherein the compound
1) inhibits the uPA-binding activity of PAI-1 as determined by adding the compound to a system comprising immobilized PAI-1 and solubilized uPA, uPA bound to PAI-1 being detected by being labelled or by means of a labelled anti-uPA antibody, or adding the compound to a system comprising immobilized uPA and solubilized PAI-1, PAI-1 bound to uPA being detected by being labelled or by means of a labelled anti-PAI-1 antibody, and/or
2) inhibits the binding of PAI-1 to uPA as determined by adding the compound to a system comprising radiolabelled PAI-1 or a derivative thereof and cells having uPA bound to the cell surface to uPA receptors and detecting any PAI-1 or derivative binding to uPA by gamma counting of the cells, and/or
3) suppresses the inhibitory activity of PAI-1 on uPA as determined by adding the compound to a system comprising PAI-1 and cells having UPA bound on the cell surface to uPA receptors and detecting any effect of PAI-1 either directly by a chromogenic uPA substrate or indirectly by adding plasminogen and measuring plasmin generation using a plasmin-specific substrate such as the fluorogenic substrate H-D-Val-Leu-Lys-7-amido-4-methylcoumarin (Bachem); the inhibitory effect of the test compound against PAI-1 in 3) is then determined by comparison of the plasmin generation curves obtained with the various concentrations of the compound with plasmin generation curves made with varying concentrations of PAI-1 added,
for preparing a composition for treating a patient who has been established to have a high risk of developing a malignant tumour or who has developed a malignant tumour by inhibiting the plasminogen activator-inhibitory activity of PAI-1 in malignant tumour tissue or potential malignant tumour tissue.

One embodiment of the invention relates to a method, wherein the compound additionally
4) inhibits the activity of PAI-1 in tumour tissue as determined by adding the compound to the malignant cells or other cells in the tumour tissue expressing PAI-1 and subsequently adding uPA, followed by measurement of uPA activity either directly by a chromogenic uPA substrate or indirectly by adding plasminogen and measuring plasmin generation.
and another embodiment of the invention relates to a method wherein the compound additionally
5) is capable of inhibiting the growth and/or invasion and/or metastasis of human malignant tumour cells when administered to a nude mouse or a nude rat which is inoculated with human malignant tumour cells which are known to invade and/or metastasize in the presence of uPA and PAI-1 and which are capable of invasion and/or metastasis in the mouse.

A discussed above, it is possible to screen for compounds useful in the above-discussed methods of and uses of the invention. It will be understood that these methods for identifying a potentially therapeutically useful substance are dependent on the actual presence of the substance. Normally, it is necessary to either purify or synthesize the candidate substance before it is subjected to the above-mentioned methods. However, since many such candidate substances could be tested before a substance which is suitably capable of interacting with e.g. PAI-1 has been identified, it is of interest to identify such substances before they are subjected to the method above, thereby diminishing the resources spent on purification and/or synthesis steps.

If the motif of binding between a known inhibitor of an inhibitor of a protease or a non-proteolytic matrix degrading enzyme can be established, the selection of compounds hitherto unknown to exhibit the same effect can be made much more easy and convenient.

Thus the invention also relates to a method for identifying and providing a compound which is useful in the methods of therapy described herein as well as for therapeutical use as described herein. The compound can be identified and provided by performing the following steps (wherein the inhibitor is PAI-1, but it will be understood that the same principles can be applied for any inhibitor of a protease or a non-proteolytic matrix-degrading enzyme):

a) identifying atomic group(s) of PAI-1 which is/are essential in the binding between PAI-1 and a substance which is a compound which has previously been identified as a substance capable of interfering with PAI-1 so as to inhibit malignant tumour growth, invasion and metastasis.

This can be done by providing mutated or truncated variants of PAI-1 and by exclusion identifying the essential atomic group(s) taking part in the binding to the known compound.

b) Providing a fragment of PAI-1 exhibiting a substantial binding to the substance, by using the information obtained in step a).

This can be done by recombinantly producing the PAI-1 fragment by the methods known to the skilled person.

c) Determining the binding free energy of the substance bound to the PAI-1 fragment provided in step b), e.g. by microcalometry, and selecting a threshold value which is at least 50% of the determined binding free energy or another binding energy value which indicates substantial interaction between a substance of a particular molecular weight and PAI-1.

As the binding free energy i.a. depends on the size of the molecules involved it will be understood that a numerically modest binding free energy is adequate if the substance is a low molecular compound, whereas a numerically high binding free energy is needed if the substance is of relatively high molecular weight. On the basis of such knowledge, the person skilled in the art will be capable of a suitable threshold value of binding free energy.

The term "substantial interaction" implies that the interaction between the substance and PAI-1 is clearly distinguishable from non-specific "background binding", i.e. that the interaction between the substance and PAI-1 is clearly distinguishable from the binding between PAI-1 and the majority of a large number of randomly selected proteins with a molecular weight comparable to that of PAI-1.

d) Co-crystallizing the PAI-1 fragment bound to the substance.

e) Performing an X-ray crystallographic analysis of the co-crystallized product obtained in step d).

f) Identifying the atomic groups of the PAI-1 fragment and of the substance taking part in the interaction between PAI-1 and the substance.

g) Providing a 3-dimensional representation (X) of the atomic groups identified in step f).

This is preferably done in a computer-graphic modelling system, of which several can be purchased commercially. One suitable implementation is the programme GRID.

h) Modifying the 3-dimensional representation (X) by exchanging, adding or removing at least one atomic group in the 3-dimensional representation provided in step g).
i) Predicting the binding free energy of the PAI-1 fragment bound to the modified version of X.
j) Selecting as a candidate substance a modified version of the substance (X) resulting in a predicted binding free energy in step i) which is higher than the threshold value selected in step c).

k) Synthesizing the candidate substance.

This step of course requires that it is possible to synthesize the compound, but normally this will be possible for a person skilled in chemistry. Carbohydrates are convenient, as these often can be prepared in one stereochemical conformation.

l) Determining the binding free energy of PAI-1 bound to the candidate substance, e.g. by microcalometry.

m) Establishing that the candidate substance results in a binding free energy determined in step 1) which is numerically higher than the threshold value selected in step c), n) Electing as the compound the candidate substance.

Just before the election of the candidate substance as the compound, the candidate substance can optionally be subjected to any of the above-described assays for in vitro and in vivo activity in order to establish that it in reality can satisfy the criteria to be expected for such a compound, i.e that it really binds to PAI-1 and that it is capable of exerting the desired effects, i.e. to confirm that the candidate substance is capable of suppressing the inhibitory activity of an inhibitor of a protease or of a non-proteolytic matrix-degrading enzyme in malignant tumour tissue or potential malignant tumour tissue.

In order to predict the binding energy in the above-indicated method, according to the invention it is especially preferred to use the following method:

Assessing the average energy difference, $$\langle \Delta V_{i-s}^{el} \rangle,$$

defined as $$\langle V_{i-s}^{el} \rangle_B - \langle V_{i-s}^{el} \rangle_A,$$

between the contribution from polar interactions to the potential energy between the substance (denoted i) and its surroundings (denoted s) in two states, one state (A) being where the substance is surrounded by solvent, the other state (B) being where the substance, bound to the site of PAI-1, is surrounded by solvent, assessing the average energy difference, $$\langle \Delta V_{i-s}^{vdw} \rangle,$$

defined as $$\langle V_{i-s}^{vdw} \rangle_B - \langle V_{i-s}^{vdw} \rangle_A,$$

between the contribution from non-polar interactions to the potential energy between the substance (denoted i) and its surroundings (denoted s) in two states, one state (A) being where the substance is surrounded by solvent, the other state (B) being where the substance, bound to the site of the receptor, is surrounded by solvent, and calculating the absolute binding free energy as an adjusted combination of the two above-mentioned average energy differences.

For more details relating to the aspects of calculating binding free energy by this method, cf. (80).

It will be understood that the compounds identified and provided by the above-indicated methods all are interesting ingredients in the therapeutical methods of the invention, and that their use in such treatment also is a part of the invention.

EXAMPLES

Example 1

Prognostic value of PAI-1 in bronchiogenic adenocarcinomas.

In non small cell lung cancer the stage of disease, including tumour size and lymph node involvement, within the specific stages, have been reported to be among the strongest prognostic factors (62,63). Even though patients with bronchogenic adenocarcinoma are surgical radically resected (stage I and II), the 5 year survival is poor, with the 5 year survival being 40% in stage I and 10% in stage II (64). Thus a means to characterize and define patients with bronchogenic adenocarcinoma and poor prognosis is needed, to select subgroups of radically resected patients for adjuvant chemotherapy. To our knowledge there is no such prognostic marker used in clinical practice today.

We have retrospectively studied the prognostic significance of uPA and PAI-1 levels as determined by ELISA in tumour extracts from patients with bronchogenic adenocarcinoma. The study includes 106 patients, all having had surgery with 81% intended radically resected.

This example describes an assay for the determination of PAI-1 in tumour extracts of bronchiogenic adenocarcinomas.

Material and Methods

Patients and tumour extracts.

Tissue from patients with bronchogenic adenocarcinoma was stored at −80° C. Tumour extracts were made by a procedure including pre-cooling the tissue in liquid nitrogen, mechanical pulverization, extraction with a buffer consisting of 75 mM potassium acetate, 0.3 M NaCl, 0.1 M L-arginine, 10 mM EDTA and 0.25% Triton X-100 pH 4.2, followed by centrifugation at 105.000 g for 1 hour. The supernatant and pellet were stored separately at −80° C.

The patients from whom the tumour tissue were obtained all had surgery at the Department of Thoracic Surgery, Bispebjerg Hospital. Patients had stage I to IIIb (New International Staging), 81% had been radically resected (macroscopic tumour free and histopathological tumour free resection edge) while the rest was found inoperable at time of thoracotomy. The pathological diagnosis, using the WHO classification, was in all cases performed by the same experienced pulmonary pathologist. Patients were followed regularly in the out-patient department until one year after resection, and if still found relapse-free no further control was planned. The median observation time was 15.6 months (range 0–73.5 months). Survival data were obtained from the central danish registry of death.

The tumour extracts were obtained from 106 lung cancer patients. PAI-1 analyses were performed on the extracts from all the patients. 70% of the patients (69 of 106), had disease stage I (T1N0 and T2N0). Histopathological tumour size, number of tumour-positive mediastinal lymph nodes, pathological diagnosis, radicality of surgery, age and overall survival were available for all patients.

PAI-1 ELISA.

PAI-1 was determined using a sandwich ELISA (18) with monoclonal catching and detecting antibodies. As catching antibody was used PAI-1 monoclonal antibody clone 1 and as detecting antibody was used PAI-1 monoclonal antibody clone 7 (PCT/DK86/00080, published as WO 87/00549). This assay detects both latent and active PAI-1, and is in addition recognizing PAI-1 bound to uPA and tPA (unpublished results, J. Grøndahl-Hansen). PAI-1 was measured in interim units by calibration with standard preparations obtained from The National Institute for Biological Standards and Control, Hertfordshire, UK. The intra- and intervariations for both assays were below 11%.

Protein content of the tumour extracts was determined by BioRad Protein Assay (Biorad, Richmond, Calif.).

Statistical methods.

For data base management and descriptive statistics, the SPSS program (Inc. SPSS, Version 4.01, 1988) was used. Life table analyses of overall survival was calculated by the product limit method (Kaplan-Meier) and the test of trends (Tarrone) was used to determine equality over strata for all patients (3 groups). Log rank test was used for patient stage I (2 groups). The Cox proportional hazards model was used for multivariate analysis of overall survival (65), using BMDP program.

Results

Characteristics of patients.

PAI-1 was measured in the supernatants of the tumour extract of bronchogenic adenocarcinomas from surgical resected patients. Table 1 shows the characteristics of the patients. The patients from whom tissue was obtained were selected for surgery intended to be radical, resulting in the majority of patients in the present material having disease stage I and II (stage according to New International Staging Classification). 81% of the patients were radically resected, and no patients were found to have distant metastases.

TABLE 1

Characterization: 106 patients with bronchiogenic adenocarcinoma

| Variable | | No. of patients N = 106 |
|---|---|---|
| Age | <65 years | 53 |
|  | >65 years | 53 |
| Sex | Males | 54 |
|  | Females | 52 |
| Tumour | T1 | 23 |
|  | T2 | 68 |
|  | T3 | 10 |
|  | T4 | 5 |
| Positive lymph nodes | N0 | 78 |
|  | N1 | 10 |
|  | N2 | 18 |
| Stage | I | 69 |
|  | II | 8 |
|  | IIIa | 23 |
|  | IIIb | 6 |
| Surgery | Radical | 86 |
|  | Not radical | 20 |

Distribution of PAI-1 levels.

FIG. 1 shows the distribution of PAI-1 in the tumour extracts. The distribution is skewed toward the lower values. The median value of PAI-1 was 0.86 interim units/mg protein (range 0.00–10.53). The cut-off levels of the lower and upper quartiles of the distribution of the PAI-1 concentrations were identified to classify patients into groups with low, medium and high concentrations of PAI-1. Within PAI-1 these levels were 0.40 InterimU/mg protein and 2.20 InterimU/mg protein.

In order to study the significance of PAI-1 in patients with local disease, the group of patients with stage I was investigated separately. In this group the median value of PAI-1 was used to separate the patients in groups with low and high concentrations; this value was 0.775 InterimU/mg protein (range 0.00–6.99).

Prognostic significance of PAI-1.

Figure 2:
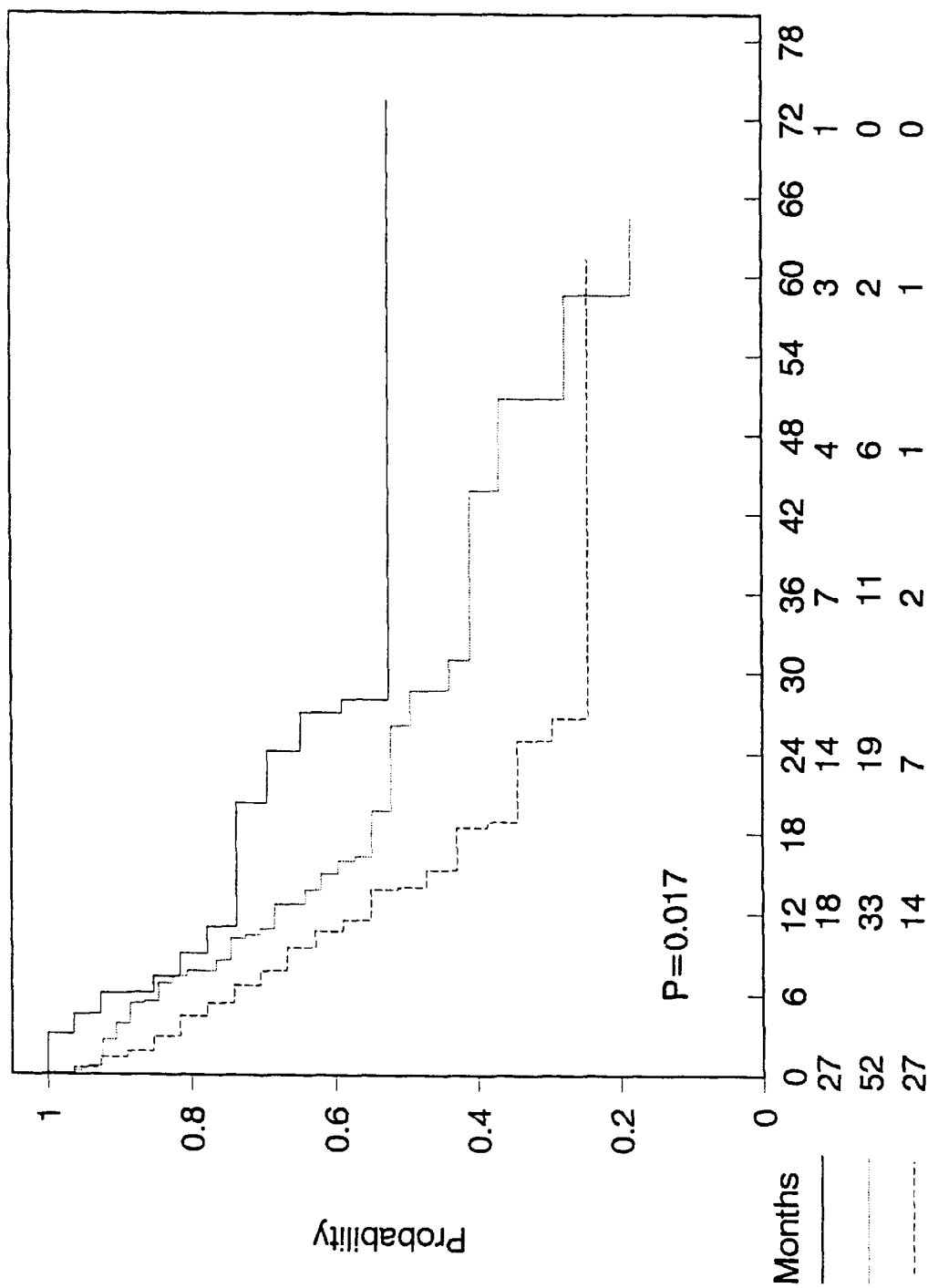
FIG. 2. Compares overall survival for patients with low, medium, and high levels of PAI-1 (Example 1).

In the 106 patients the overall survival was compared for patients with low, medium and high levels of PAI-1. As seen in FIG. 2, overall survival was significantly better for patients with low PAI-1 concentration, than for patients with medium or high concentration (P=0.017, Tarone test of trends). The prognostic significance of PAI-1 was studied by univariate analysis. PAI-1 was found to have an impact on death hazard with a relative risk of 1.6 for low versus medium and 2.4 for low versus high (95% confidence interval 1.1–2.3 and 1.7–3.5, respectively).

Association of PAI-1 with other prognostic variables.

The association between tumour PAI-1 level and other prognostic variables was studied using the $X^2$ test. As Table 2 illustrates there was no significant association between PAI-1 and other prognostic factors, such as age, disease stage, sex, tumour size or number of involved lymph nodes.

TABLE 2

$X^2$ test for association between PAI-1 tumour extracts and other variables in patients with bronchiogenic adenocarcinomas.

| Variable | Correlation with PAI-1 P-value |
|---|---|
| Age | 0.63 |
| Sex | 0.16 |
| Stage | 0.21 |
| Radicality | 0.20 |
| Tumour size | 0.59 |
| Lymph nodes | 0.22 |

Multivariate analysis.

To compare the prognostic significance of PAI-1 level with that of other parameters, multivariate analysis was performed for the 104 patients for whom full data were available (Table 3). Variables were eliminated from the model singly in a backwards fashion and reincluded only if the P-value was less than 0.05. This left PAI-1 and stage as the only two parameters. Using this analysis tumour PAI-1 level was found to be a statistically significant independent variable of overall survival with a relative risk of 1.5 for low versus medium and 2.3 for low versus high (95% confidence interval 1.1–2.2 and 1.6–3.3, respectively).

TABLE 3

Multivariate Cox regression analysis of 106 patients with bronchiogenic adenocarcinoma

| Variable | Overall survival Multivariate P-value | Relative risk |
|---|---|---|
| Stage | >0.005 | 2.3 |
| PAI-1 |  |  |
| low vs. med. | 0.05 | 1.5 (1.1–2.2) |
| low vs. high | 0.005 | 2.3 (1.6–3.3) |

Prognostic significance of tumour PAI-1 within patient subgroups.

Figure 3:
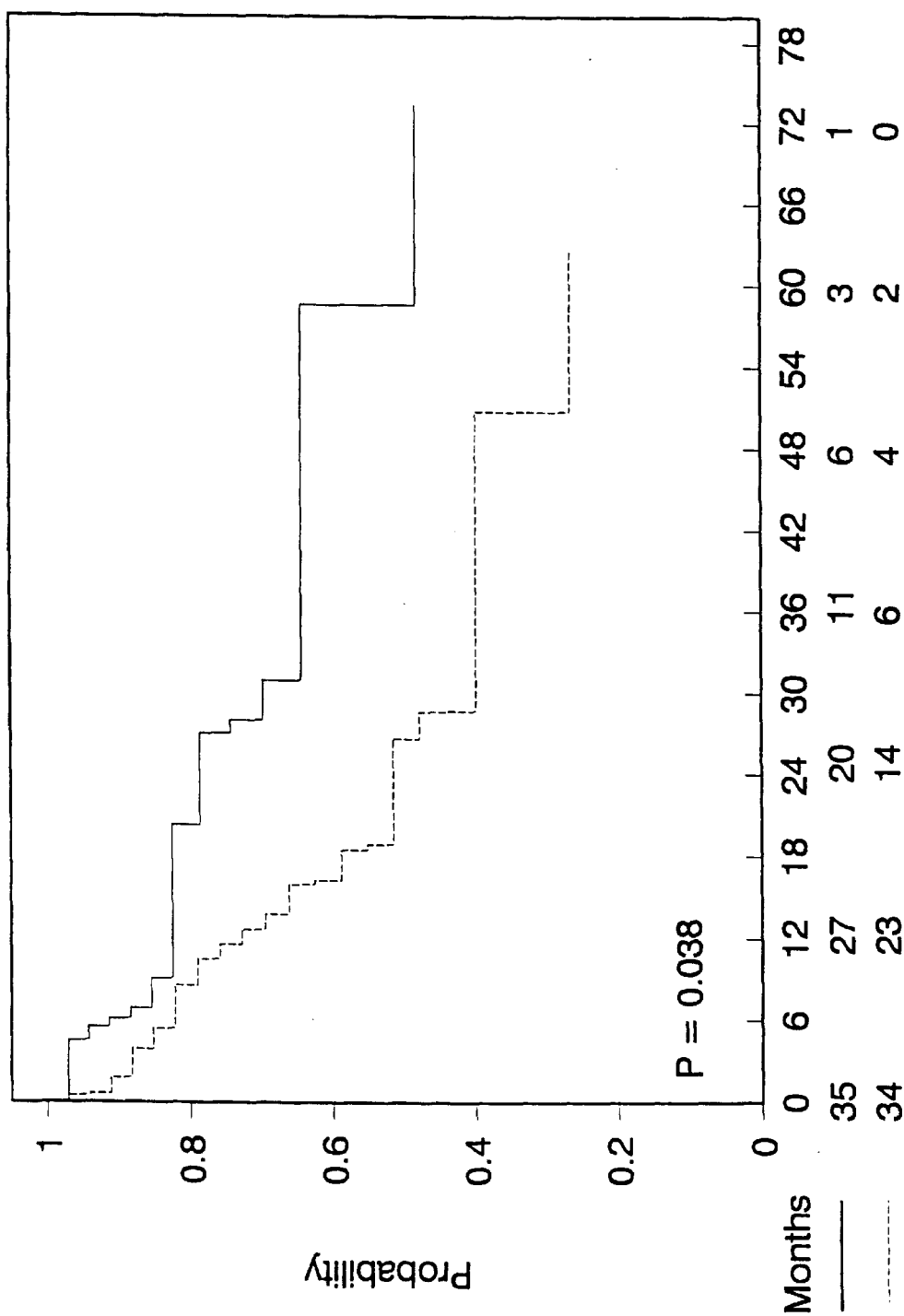
FIG. 3. Compares overall survival for stage I disease patients with low or high levels of PAI-1 (Example 1).

Regarding patients with stage I disease overall survival was compared for patients with levels below the median values and those with levels above. As shown in FIG. 3 there was a significant association between PAI-1 and overall survival (P=0.037).

Discussion

This retrospective study of 106 patients with bronchogenic adenocarcinoma, stage I to IIIb, indicates that high levels of PAI-1 in tumour extract supernatants are associated with short overall survival with statistical significance. In a multivariate analysis including all patients and factors such as age and stage, tumour PAI-1 was a significantly independent prognostic factor for overall survival.

In patients with localized disease (stage I and II) the 5 year survival is 40% in the subgroup with stage I and 10% in the subgroup with stage II (64). Determination of PAI-1 levels may be a useful prognostic marker to select radically resected patients with bronchogenic adenocarcinoma and poor prognosis for adjuvant treatment. The present study was limited to adenocarcinomas within the group of Non Small Cell Lung Cancer (NSCLC) in a relatively small number of patients. Hence the prognostic value of PAI-1 should be further evaluated in larger materials and within other subgroups of NSCLC. Also, the prognostic value of PAI-1 in other types of cancer might be evaluated in a similar manner (78).

Example 2

Predictive value of PAI-1 measurements in bronchiogenic adenocarcinomas.

As shown in Example 1, a proportion of lung cancer patients have high levels of PAI-1 in their tumours which predict a poor prognosis. Accordingly, patients with high PAI-1 levels will be candidates for a treatment aiming at inhibiting the binding of PAI-1 to uPA. This example describes a predictive assay to identify patients who potentially will benefit from such a treatment.

Material and Methods

Patients.

Patients with bronchiogenic adenocarcinoma stage I or II referred for adjuvant therapy subsequent to radical resection of their lung tumours.

Tumour Extraction.

Tumour tissue from the patients with bronchogenic adenocarcinoma is stored at −80° C. Tumour extracts are made by a procedure including pre-cooling the tissue in liquid nitrogen, mechanical pulverization, extraction with a buffer consisting 75 mM potassium acetate, 0.3 M NaCl, 0.1 M L-arginine, 10 mM EDTA and 0.25% Triton X-100 pH 4.2, followed by centrifugation at 105.000 g for 1 hour. The supernatant and pellet are stored separately at −80° C.

PAI-1 Elisa.

PAI-1 is determined using a sandwich ELISA (18) with monoclonal catching and detecting antibodies. As catching antibody is used PAI-1 monoclonal antibody clone 1 and as detecting antibody is used PAI-1 monoclonal antibody clone 7 (WO 87/00549). This assay detects both latent and active PAI-1, and is in addition recognizing PAI-1 bound to uPA and tPA (unpublished results, J. Grøndahl-Hansen). PAI-1 is measured in interim units by calibration with standard preparations obtained from The National Institute for Biological Standards and Control, Hertfordshire, UK. The intra- and intervariations for both assays are below 11%. Protein content of the tumour extracts is determined by BioRad Protein Assay (Biorad, Richmond, Calif.).

Treatment.

All patients entering this study will receive the antiprotease inhibitor treatment. Clinical responses will be recorded according to standard procedures (EORTC). Patients will be post-stratified according to tumour PAI-1 content (patients with PAI-1 levels above versus below the already established median value of 0.775 InterimU/mg protein (Example 1)) and number and duration of objective responses will be compared between the two groups of patients.

Example 3

In Situ Hybridization for PAI-1 mRNA and Immunostaining of PAI-1 Protein in Human Lung Cancer Immunohistochemistry Cryostat sections from 24 samples of pulmonary carcinoma were used for immunohistochemistry. These included 14 cases of squamous cell carcinoma, 5 cases of adenocarcinomas, 3 cases of mixed tumours (adenocarcinoma and squamous cell carcinoma) and 3 cases of large cell undifferentiated carcinoma. Adjacent normal mucosal tissue resected at time of surgery was obtained from 3 of the patients. Monoclonal anti-human PAI-1 antibodies (clones 1 and 2) were used for immunohistochemical stainings. An irrelevant monoclonal antibody (m-anti-TNP) was used as a negative control. The two monoclonal antibodies have previously been shown to be directed against two different epitopes on PAI-1. 5 μm cryostat sections were subjected to a conventional APAAP (Alkaline Phosphatase-Anti-Alkaline Phosphatase) method as described previously (45).

In Situ Hubridization 10 of the above samples were tested by in situ hybridization for the presence of PAI-1 mRNA by a method described in detail previously (42). In brief, 35-S labelled RNA probes, transcribed from a 504 base pair PstI-PstI fragment of human PAI-1 cDNA were applied to deparaffinized, proteinase K-digested sections, hybridized overnight at 48° C., then RNAse-treated and washed in high stringency buffer before being overlaid with photographic emulsion. Slides were developed after 10–14 days of exposure.

Results

Imunohistochemistry

In all cases investigated an identical staining pattern with the two antibodies was found. Monoclonal anti-TNP antibody consistently gave no staining. In all samples the presence of PAI-1 antigen throughout the stromal parts of cancerous tissue could be demonstrated. Individual fibroblast-like stromal cells were often strongly positive, but often the staining was markedly diffuse and reticulate, following the collagen fibrils. In 11 cases, all of which were of the squamous type, a number of tumour cells were also positive for PAI-1. Three samples of adjacent normal mucosal tissue contained no PAI-1 immunoreactivity.

Figure 4:
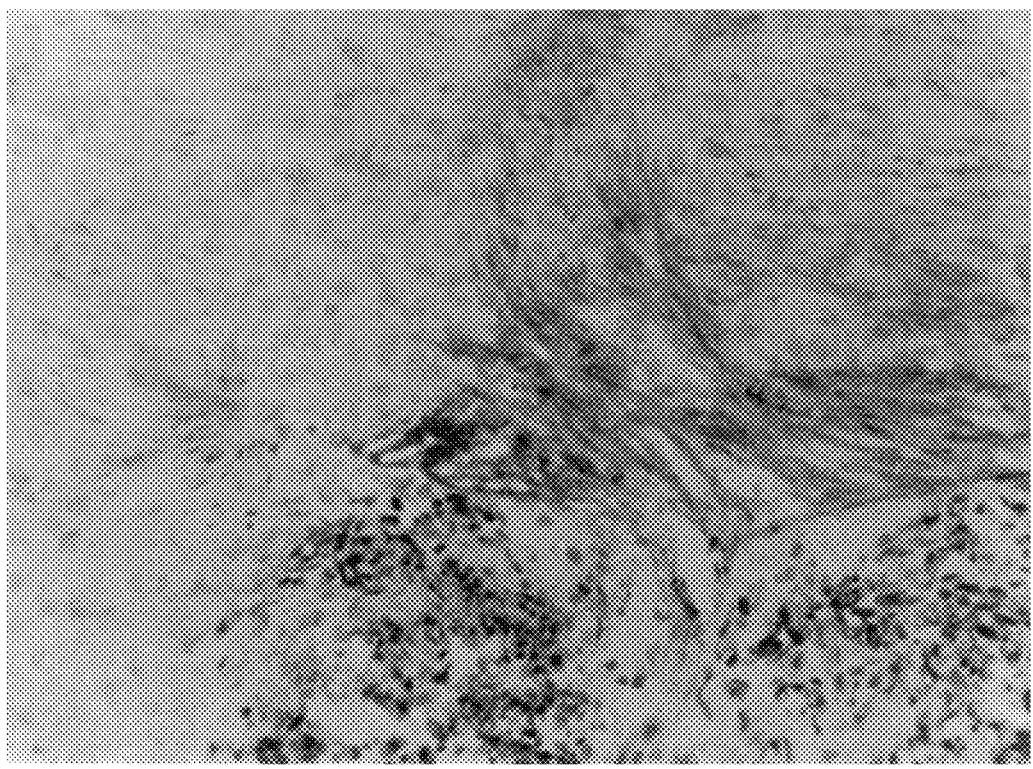
FIG. 4. Shows immunostaining for PAI-1 on a specimen of lung cancer tissue (Example 3).

FIG. 4 shows immunostaining for PAI-1 on a specimen of lung cancer tissue. Note the intense signal in the stromal compartment.

In Situ Hybridization.

Routinely processed paraffin-embedded specimens from 10 of the 24 cases were investigated by in situ hybridization for the presence of mRNA for PAI-1. In all of these specimens a pattern of gene expression for PAI-1 very similar to the patterns of immunostaining was observed.

Example 4

Screening scheme

The following examples describes an example of a compound screening scheme comprising various successive steps which is established to identify compounds which can be used to inhibit the interaction between PAI-1 and uPA and thereby be used as drugs to inhibit the invasive and metastatic process.

The initial screening of the compounds is performed e.g. by use of the below described compound screening ELISA and if the compound show inhibitory effect, the further screening of compounds is performed using the next steps in the scheme (Examples 5 and 6).

Compound screening ELISA for use in the screening of compounds capable of inhibiting PAI-1/uPA interaction A two antibody sandwich ELISA assay is developed for screening compounds for their capability to inhibit the interaction between PAI-1 and uPA in solution. The effect of the compound to be screened to inhibit the interaction can be tested at various concentration. In the present case, the compound X is tested and the effect of X on the interaction is examined. As an example, X is PAI-1 monoclonal antibody which inhibits PAI-1 inhibition of uPA (WO 87/00549).

Materials
1) 96-well plates (flat-bottom high binding capacity, NUNC).
2) Unlabelled purified PAI-1 monoclonal antibody e.g. clone 1 (WO 87/00549).
3) Purified anti-uPA clone 5 (66) labelled with biotin.
4) Horseradish peroxidase-conjugated (HRP) avidin.
5) Affinity purified PAI-1 (SDS-activated).
6) recombinant uPA (activated).
7) Compound X
8) PBS buffer, pH 7.4 (PBS)
9) PBS+0.1 Tween 20, pH 7.4 (PBS/Tween)
10) Blocking buffer: 1% skimmed milk powder (SMP) in PBS
11) Citrate buffer: 0.1 M citrate, pH 5.0.
12) Substrate solution: 1,2-Phenylenediamine dihydrochloride (OPD) tablets in citrate buffer, e.g. 3 OPD tablets in 15 ml of citrate.
13) Stop buffer: 1M $H_2SO_4$.

Procedure
1) Coat the wells with 100 µl of PAI-1 antibody (20 µg/ml) diluted in 0.1 M $Na_2CO_3$.
2) Incubate overnight at 4° C.
3. Wash the wells 5× in PBS/Tween.
4) Block the remaining active sites in the wells with 1% SMP/PBS, 200 µl/well, for at least 1 hour at RT. Gentle shaking.
5) Wash as in step 3).
6) Add 100 µl of PAI-1 (20 ng/ml).
7) Incubate with gentle shaking for 1 hour at RT.
8) Wash as in step 3).
9) Add a mixture of 50 µl of uPA (10 ng/ml) and 50 µl of blocking buffer or a mixture of 50 µl of uPA (10 ng/ml) and 50 µl of serial dilution of X.
10) Incubate as in step 7).
11) Wash as in step 3).
12) Add 100 µl of biotinylated anti-uPA clone 5 (2 µg/ml).
13) Incubate as in step 7).
14) Wash as in step 3).
15) Add 100 µl of HRP-avidin diluted 1:5000 in SMP/PBS/Tween.
16) Incubate as in step 7).
17) Wash as in step 3).
18) Wash 1× in distilled water.
19) Add 100 µl/well of substrate solution.
20) Stop the reaction with 100 µl/well of 1M $H_2SO_4$, when bright yellow colour appears.
21) Read on an ELISA-reader with 490 nm filter with 540 nm filter as a background reference.

The ELISA assay described above can be constructed in a similar manner with uPA antibody as catching antibody and biotinylated PAI-1 antibody or antibodies as detecting anti-body(ies).

Candidate drugs for inhibiting PAI-1 binding to uPA can be found by screening drug libraries consisting of naturally occurring compounds, small molecules and peptides. Also random peptide bacteriophage display or synthetic peptide libraries may be used.

Example 5
Screening of compounds for their capability to inhibit the binding of PAI-1 to uPA on the cell surface The capability of a compound to inhibit the binding of PAI-1 to uPA is suitably examined as a step of the scheme aiming to identify and characterize new potential drugs. By replacing the monoclonal PAI-1 antibody clone 2 (WO 87/00549) with the compound under test in various concentrations, the capability of the compound to inhibit the binding of PAI-1 to uPA and thereby preventing inactivation of uPA on the cell surface can be evaluated.

The assay is based on that described for determining the inhibition of receptor bound uPA by plasminogen activator inhibitors (61). U937 cells ($2\times10^7$/ml) are incubated with uPA (1.4 nM), after washing in 0.05 M glycine-HCl, 0.1 M NaCl, pH3.0 to remove endogenously bound uPA. The cells are then washed to remove excess uPA and incubated in 10-mm plastic fluorometer cuvettes at 37° C. at a final concentration of $1\times10^6$/ml, with plasminogen (20 µg/ml) and the plasmin-specific fluorogenic substrate H-D-Val-Leu-Lys-7-amido-4-methylcoumarin (Bachem) in 0.05 M Tris-HCl, 0.1 M NaCl, pH7.4. PAI-1 is included in these incubations at a concentration of 1 µg/ml, after pre-incubation with varying concentrations of the test compound or antibody. The increase in fluorescence due to hydrolysis of the substrate is measured at 1-minute intervals for 15 minutes, and plasmin generation determined form the rate of change in fluorescence intensity. The inhibitory effect of the test compound or antibody against PAI-1 is then determined by comparison of the plasmin generation curves obtained with the various concentrations of the compound with plasmin generation curves made with varying concentrations of PAI-1 (0, 0.25, 0.5, 0.75 and 1 µg/ml). Thus a percentage inhibitory effect is obtained at any chosen concentration of the compound.

Example 6
Screening of compounds for their capability to inhibit the invasive and metastatic process of human cancer cells in nude mice The last step in the screening of compounds which have been shown in the above described previous steps of the compound screening scheme to inhibit the interaction between PAI-1 and uPA which thereby are potential compounds to be used as drugs to inhibit the progression of cancer, is to evaluate the effect of the compound to inhibit growth as well as the invasive and metastatic process in vivo. A mouse model in which the invasive and metastatic process of human cancer cells can be measured has been developed to evaluate this effect (PCT/DK92/00306).

This example describes an experimental study using neutralizing monoclonal PAI-1 antibodies as a means to inhibit formation of metastasis of a human breast cancer xenograft in nude mice.

Method
Cell line

The human breast cancer cell line MDA-MB-231 BAG was routinely propagated in DMEM with 5% Fetal Calf Serum. These cells have been transduced with the lacZ gene as previously described (67). Cells for nude mouse experiments were harvested using a cell scraper instead of using enzymes.

Retroviral transduction

To visualize the metastatic tumours, the human cancer cell type to be used in the assay is labelled by transducing or transfecting the cells with a LacZ gene whereby the cells can be visualized by X-gal staining. This transduction has previously been performed by (67) using human MDA-MB-231 and human MDA-MB-435 breast cancer cells. The lacZ gene codes for β-D-galactosidase, the activity of which can be detected by staining with the chromogenic substrate 5-bromo-4-chloro-3-indolyl-β-D-galactopyranoside (X-gal), which gives a dark blue reaction. Thereby also microscopic metastatic tumours can be detected.

The transduction of the human cancer cells chosen can be performed as described in (67).

Mice

Nude female mice 6–8 weeks-old nu/nu META/Bom (Bomholtgaard, Denmark) were used. The mice were kept in laminar flow clean benches and all equipment used was autoclaved.

Antibodies

PAI-1 monoclonal antibodies clone 2 (WO 87/00549), which neutralizes the inhibitory effect of PAI-1 (Rømer, personal communication), and clone 3 (WO 87/00549), which does not influence the inhibitory activity of PAI-1 (Rømer, personal communication), were used.

Pharmacokinetics of the compound

The pharmacokinetic characteristics of the compound or antibody to be screened should be clarified in order to administer and retain the compound or antibody in an effective concentration in the mouse.

The administration of the compound or antibody to be screened depends on the chemical nature of the compound or antibody and may be performed by interperitoneal injection or subcutaneous injection, by oral administration or local application.

Therefore, mice were injected intraperitoneally with a single dose of either PAI-1 monoclonal antibody clone 2 or clone 3 (WO 87/00549) and at different time points after this injection mice were bleed and serum were tested for PAI-1 antibody content. Furthermore, in the experiment with the tumor-bearing animals, serum was obtained from all anti-PAI-1 antibody treated animals by tail vein bleeding every week. The concentration of PAI-1 antibodies were analyzed with an ELISA.

Pretreatment of mouse and transduced cancer cells

It may be an advantage to pretreat the mouse with the compound or antibody to be screened before injecting the transduced cancer cells in order to obtain satisfactory concentrations of the compound or antibody. Furthermore, the transduced cancer cells to be injected into the mouse may be preincubated in a solution containing the compound or antibody in order to ensure a contact between the cells and the compound or antibody. Normally several experiments in which this pretreatment is varied or excluded should be performed in order to clarify and ascertain the overall effect of the compound or the antibody.

Thus, a total number of $2 \times 10^6$ MDA-MB-231 BAG cells were inoculated subcutaneously into each flank of the animals. The tumor cells were always placed inferior to the thoracic wall. One day before cell inoculation 250 μg of antibodies were injected into the mice. Based on pharmacokinetic studies (FIG. 5A and 5B, which shows a pharmacokinetic investigation of anti-PAI-1 monoclonal antibody clone 2 and clone 3, respectively, in nude mice injected intraperitoneally with 250 μg antibody on day 0) of the antibodies used, a second injection of 250 μg antibody was given every week. The mice were sacrificed 6 weeks after cell inoculation.

Measurement of tumour growth

The growth of the tumours should be measured in order to elucidate whether the compound under test affects the growth of the tumour in addition to the possible effect on the invasive and metastatic process.

Hence, the xenografted tumours were measured twice weekly in two dimensions and tumor growth curves were constructed on the basis of a transformed Gompertz function.

Duration of the screening assay

The duration of the assay depends on the nature of the compound or antibody and on the effect of the compound or antibody on the growth and invasive and metastatic process.

Examination of xenotransplanted human MDA-MB-231 BAG tumors for human PAI-1

The xenotransplanted tumors were surgically removed from the animals and examined by Northern blotting for the presence of human PAI-1 mRNA and by ELISA for the presence of human PAI-1 protein.

Examination of xenotransplanted MDA-MB-231 BAG tumors for mouse PAI-1

The xenotransplanted tumors were surgically removed from the animals and examined for mouse PAI-1 mRNA by in situ hybridization with a mouse specific probe.

Evaluation of the invasive and metastatic process

The effect of the compound or antibody on the invasive and metastatic process and on the growth of the tumour can be evaluated locally and/or in the lungs, the lymph nodes and in the interperitoneal cavity utilizing the very distinct differentiation between human cells and mouse cells rendered possible by the staining (67–69).

Accordingly, at autopsy lungs were excised from each animals and the lungs were processed with X-gal according to the method described by Brünner et al (67). To confirm the presence of human tumor cell metastases, blue areas from various lungs were fixed in 4% formalin and processed for routine histology. If a lung presented one or more blue areas it was registered as positive for metastatic lesion. Alternatively, an ELISA for β-D-galactosidase as described by Fujiwara et al (79), could be used as an objective measurement of metastatic spread.

Results

Results of the examination of the xenotransplanted tumors

MDA-MB-231 BAG tumors expressed abundant mRNA and protein for human PAI-1. By in situ hybridization, the xenotransplanted tumor was shown to express mouse PAI-1 in the stromal cells including the vessels infiltrating the human tumor cells.

Pharmacokinetics

Figure 5A:
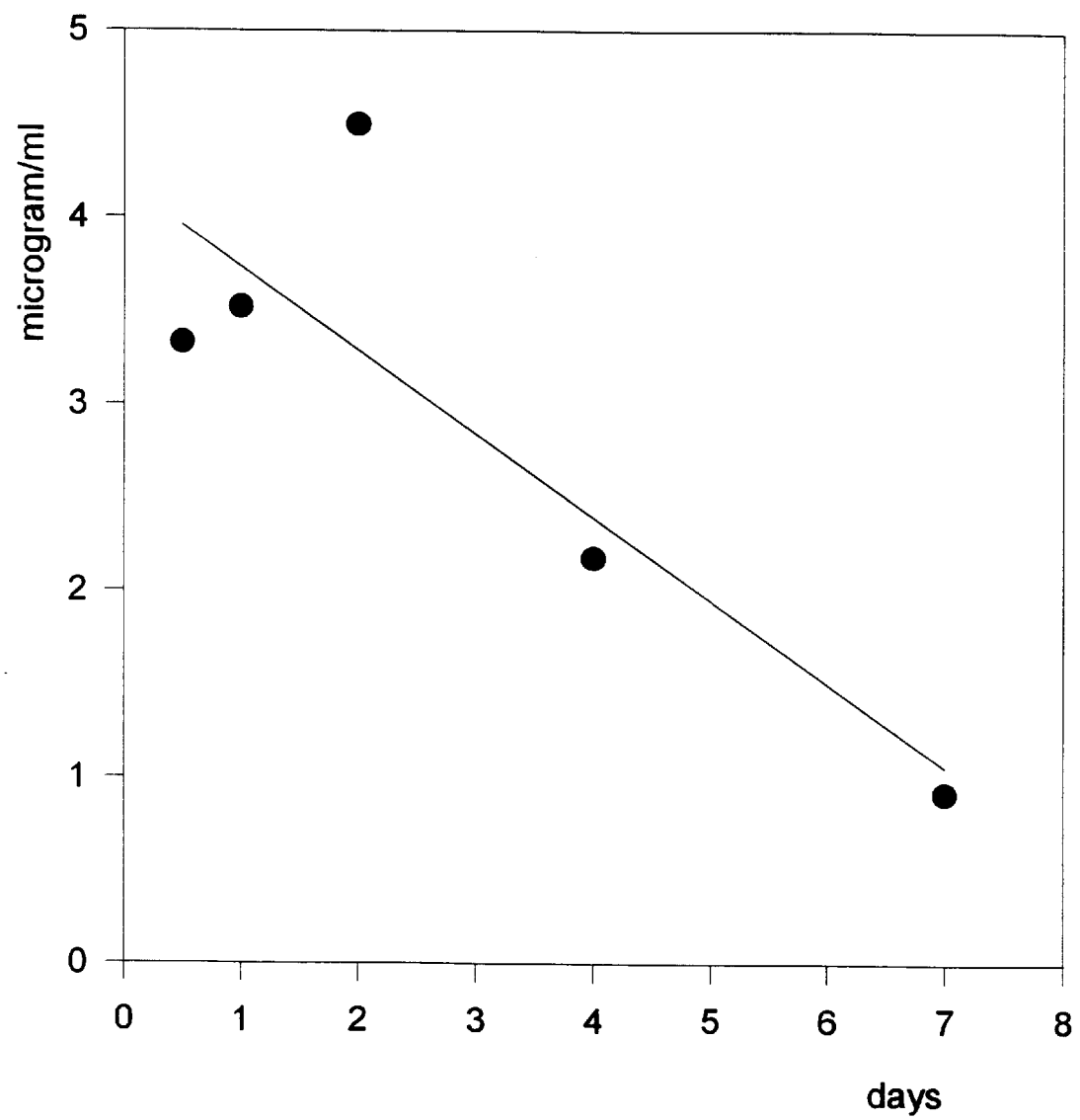
FIG. 5. Reports the time trend of anti-PAI-1 antibody levels in vivo for clone 2 (FIG. 5A) and clone 3 (FIG. 5B) (Example 6).
Figure 5B:
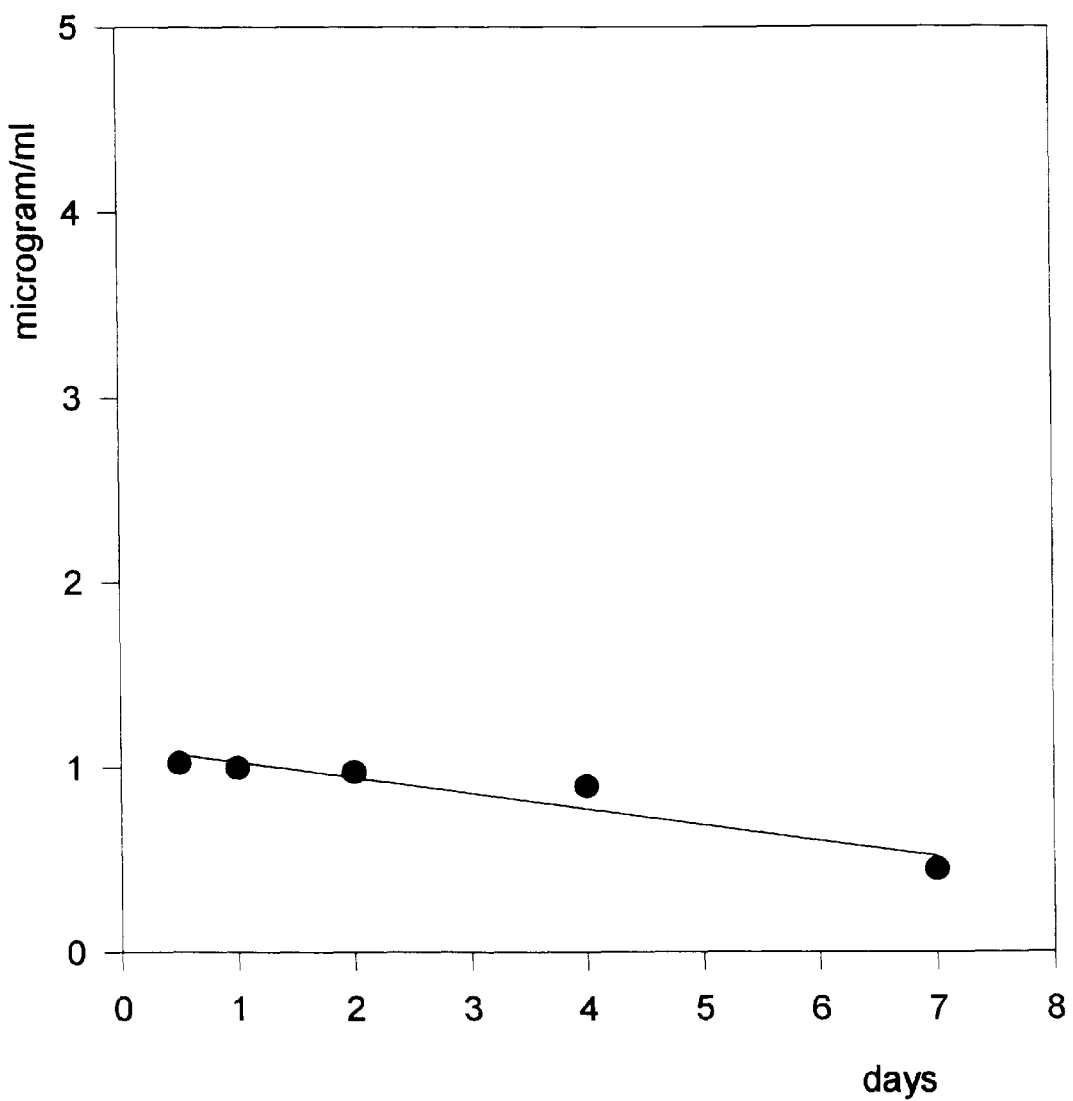

The half-life of PAI-1 antibody clone 2 was estimated to approximately 4 days and for PAI-1 clone 3 approximately 6 days (FIG. 5A and 5B).

Inhibition of tumor cell metastasis

As seen from Table 4, 9 out of 10 untreated control animals had lung metastases. Injection with the control antibody, PAI-1 antibody clone 3, resulted in a slight reduction in the number of animals with lung metastases (6 out of 10) while injection with PAI-1 antibody clone 2 significantly abolished formation of lung metastases with only 1 out of 10 mice having lung metastases.

Metastatic spread of human cancer cells was confirmed by the presence of cancer cells in the blue spots, as determined by conventional histologic examinations.

In a similar manner, other potential PAI-1 inhibitors can be tested in this model.

TABLE 4

| TREATMENT | LUNG METASTASES |
| --- | --- |
| Untreated control | 9/10 |
| PAI-1 clone 3 | 6/10 |
| PAI-1 clone 2 | 1/10 |

Effect of PAI-I antibodies on tumor growth

Figure 6:
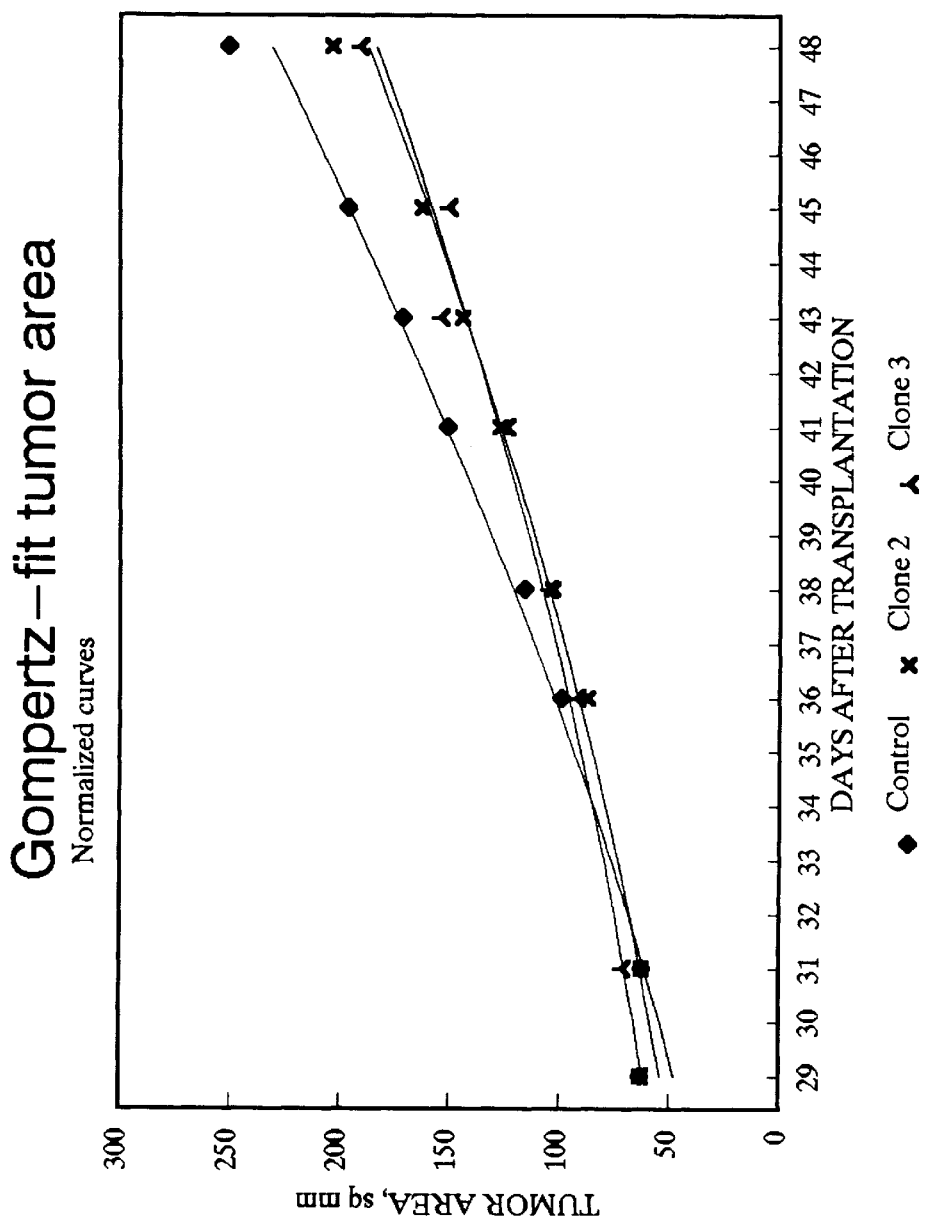
FIG. 6. Reveals the effect of anti-PAI-1 antibodies on area growth of a xenotransplanted tumor (Example 6).

Examination of the effect of the PAI-1 antibodies on tumor growth showed that both antibodies as compared to untreated controls, induced a slight but non significant retardation of tumor growth (FIG. 6 which shows tumour area growth curves of human breast carcinoma cell line MDA.MB-231 BAG injected subcutaneously into female nu/nu META/BOM mice on day 0).

After appropriate toxicological studies an active compound should be tested in phase I and phase II trials.

REFERENCES

1. Danø, K., Andreasen, P. A., Grøndahl-Hansen, J., Kristensen, P., Nielsen, L. S., and Skriver, L. Plasminogen Activators, Tissue Degradation and Cancer. Adv. Cancer Res., 44: 139–266, 1985.
2. Patthy, L. Evolution of the Proteases of Blood Coagulation and Fibrinolysis by Assembly from Modules. Cell, 41: 657–663, 1985.
3. Marcotte, P. A., Kozan, I. M., Dorwin, S. A., and Ryan, J. M. The Matrix Metalloproteinase Pump-1 Catalyzes Formation of Low Molecular Weight (Pro)urokinase in Cultures of Normal Human Kidney Cells. J. Biol. Chem., 267: 13803–13806, 1992.
4. Murphy, G., Ward, R., Gavrilovic, J., and Atkinson, S. Physiological Mechanisms for Metalloproteinase Activation. In: H. Birkedal-Hansen, Z. Werb, H. Welgus and H. Van Wart (eds.), Matrix Metalloproteinases and Inhibitors, pp. 245–255, Stuttgart: Gustav Fischer Verlag. 1992.
5. Lyons, R. M., Gentry, L. E., Purchio, A. F., and Moses, H. L. Mechanism of Activation of Latent Recombinant Transforming Growth Factor $\beta1$ by Plasmin. J. Cell Biol., 110: 1361–1367, 1990.
6. Sato, Y. and Rifkin, D. B. Inhibition of Endothelial Cell Movement by Pericytes and Smooth Muscle Cells: Activation of a Latent Transforming Growth Factor-$\beta1$-like Molecule by Plasmin during Co-culture. J. Cell Biol., 109: 309–315, 1989.
7. Campbell, P. G., Novak, J. F., Yanosick, T. B., and McMaster, J. H. Involvement of the Plasmin System in Dissociation of the Insulin-Like Growth Factor-Binding Protein Complex. Endocrinology, 130: 1401–1412, 1992.
8. Saksela, O. and Rifkin, D. B. Release of Basic Fibroblast Growth Factor-Heparan Sulfate Complexes from Endothelial Cells by Plasminogen Activator-Mediated Proteolytic Activity. J. Cell Biol., 110: 767–775, 1990.
9. Laiho, M. and Keski-Oja, J. Growth Factors in the Requlation of Pericellular Proteolysis: A Review. Cancer Research, 49: 2533–2553, 1989.
10. Liotta, L. A. Tumour Invasion and Metastases-Role of the Extracellular Matrix: Rhoads Memorial Award Lecture. Cancer Research, 46: 1–7, 1986.
11. Ossowski, L. and Reich, E. Antibodies to Plasminogen Activator Inhibit Human Tumor Metastasis. Cell, 35: 611–619, 1983.
12. Ossowski, L. In Vivo Invasion of Modified Chorioallantoic Membrane by Tumor Cells: the Role of Cell Surface-bound Urokinase. J. Cell Biol., 107: 2437–2445, 1988.
13. Mignatti, P., Robbins, E., and Rifkin, D. B. Tumor Invasion Through the Human Amniotic Membrane: Requirement for a Proteinase Cascade. Cell, 47: 487–498, 1986.
14. Reich, R., Thompson, E. W., Iwamoto, Y., Martin, G. R., Deason, J. R., Fuller, G. C., and Miskin, R. Effects of Inhibitors of Plasminogen Activator, Serine Proteinases, and Collagenase IV on the Invasion of Basement Membranes by Metastatic Cells. Cancer Research, 48: 3307–3312, 1988.
15. Hearing, V. J., Law, L. W., Corti, A., Appella, E., and Blasi, F. Modulation of Metastatic Potential by Cell Surface Urokinase of Murine Melanoma Cells. Cancer Research, 48: 1270–1278, 1988.
16. Vassalli, J. D., Baccino, D., and Belin, D. A Cellular Binding Site for the Mr 55,000 Form of the Human Plasminogen Activator, Urokinase. J. Cell Biol., 100: 86–92, 1985.
17. Cubellis, M. V., Nolli, M. L., Cassani, G., and Blasi, F. Binding of Single-chain Prourokinase to the Urokinase Receptor of Human U937 Cells. J. Biol. Chem., 261: 15819–15822, 1986.
18. Behrendt, N., Rønne, E., Ploug, M., Petri, T., Løber, D., Nielsen, L. S., Schleuning, W. D., Blasi, F., Appella, E., and Danø, K. The Human Receptor for Urokinase Plasminogen Activator. J. Biol. Chem., 265: 6453–6460, 1990.
19. Roldan, A. L., Cubellis, M. V., Masucci, M. T., Behrendt, N., Lund, L. R., Danø, K., Appella, E., and Blasi, F. Cloning and expression of the receptor for human urokinase plasminogen activator, a central molecule in cell surface, plasmin dependent proteolysis. EMBO J., 9: 467–474, 1990.
20. Behrendt, N., Ploug, M., Patthy, L., Houen, G., Blasi, F., and Danø, K. The Ligand-binding Domain of the Cell Surface Receptor for Urokinase-type Plasminogen Activator. J. Biol. Chem., 266: 7842–7847, 1991.
21. Møller, L. B. Structure and Function of the Urokinase Receptor. Blood Coagulation and Fibrinolysis, 4: 1993.
22. Ploug, M., Rønne, E., Behrendt, N., Jensen, A. L., Blasi, F., and Danø, K. Cellular Receptor for Urokinase Plasminogen Activator. Carboxyl-terminal processing and membrane anchoring by glycosyl-phosphatidylinositol. J. Biol. Chem., 266: 1926–1933, 1991.
23. Høyer-Hansen, G., Rønne, E., Solberg, H., Behrendt, N., Ploug, M., Lund, L. R., Ellis, V., and Danø, K. Urokinase plasminogen activator cleaves its cell surface receptor releasing the ligand-binding domain. J. Biol. Chem., 267: 18224–18229, 1992.
24. Ellis, V., Behrendt, N., and Danø, K. Plasminogen Activation by Receptor-bound Urokinase. J. Biol. Chem., 266: 12752–12758, 1991.
25. Rønne, E., Behrendt, N., Ellis, V., Ploug, M., Danø, K., and Høyer-Hansen, G. Cell-induced Potentiation of the Plasminogen Activation System is Abolished by a Monoclonal Antibody that Recognizes the NH-terminal Domain of the Urokinase Receptor. FEBS. Letters, 288: 233–236, 1991.
26. Ellis, V., Pyke, C., Eriksen, J., Solberg, H., and Danø, K. The Urokinase Receptor: Involvement in Cell Surface Proteolysis and Cancer Invasion. Ann. N. Y. Acad. Sci., 667: 13–31, 1992.
27. Ichinose, A., Fujikawa, K., and Suyama, T. The Activation of Pro-Urokinase by Plasma Kallikrein and its Inactivation by Thrombin. J. Biol. Chem., 261: 3486–3489, 1986.
28. Kobayashi, H., Schmitt, M., Goretzki, L., Chucholowski, N., Calvete, J., Kramer, M., Günzler, W.

A., Janicke, F., and Graeff, H. Cathepsin B Efficiently Activates the Soluble and the Tumor Cell Receptor-bound Form of the Proenzyme Urokinase-type Plasminogen Activator (Pro-uPA). J. Biol. Chem., 266: 5147–5152, 1991.

29. Lund, L. R., Rømer, J., Rønne, E., Ellis, V., Blasi, F., and Danø, K. Urokinase-receptor biosynthesis, mRNA level and gene transcription are increased by transforming growth factor β1 in human A549 lung carcinoma cells. EMBO J., 10: 3399–3407, 1991.

30. Lund, L. R., Rønne, E., Roldan, A. L., Behrendt, N., Rømer, J., Blasi, F., and Danø, K. Urokinase Receptor mRNA Level and Gene Transcription Are Strongly and Rapidly Increased by Phorbol Myristate Acetate in Human Monocyte-like U937 Cells. J. Biol. Chem., 266: 5177–5181, 1991.

31. Andreasen, P. A., Georg, B., Lund, L. R., Riccio, A., and Stacey, S. N. Plasminogen activator inhibitors: hormonally regulated serpins. Mol. Cell. Endocrinol., 68: 1–19, 1990.

32. Mimuro, J. and Loskutoff, D. J. Purification of a Protein from Bovine Plasma that Binds to Type 1 Plasminogen Activator Inhibitor and Prevents its Interaction with Extracellular Matrix. J. Biol. Chem., 264: 936–939, 1989.

33. Scott, R. W., Bergman, B. L., Bajpai, A., Hersh, R. T., Rodriquez, H., Jones, B. N., Barreda, C., Watts, S., and Baker, J. B. Protease Nexin. J. Biol. Chem., 260: 7029–7034, 1985.

34. Cubellis, M. V., Wun, T. C., and Blasi, F. Receptor-mediated internalization and degradation of urokinase is caused by its specific inhibitor PAI-1. EMBO J., 9: 1079–1085, 1990.

35. Estreicher, A., Mühlhauser, J., Carpentier, J. L., Orci, L., and Vassalli, J. D. The Receptor for Urokinase Type Plasminogen Activator Polarizes Expression of the Protease to the Leading Edge of Migrating Monocytes and Promotes Degradation of Enzyme Inhibitor Complexes. J. Cell Biol., 111: 783–792, 1990.

36. Nykjær, A., Petersen, C. M., Møller, B., Jensen, P. H., Moestrup, S. K., Holtet, T. L., Etzerodt, M., Thøgersen, H. C., Munch, M., and Andreasen, P. A. Purified Alpha 2-Macroglobulin Receptor/LDL Receptor-Related Protein Bind Urokinase. Plasminogen Activator Inhibitor Type-1 Complex. Evidence that the Alpha 2-Macroglobulin Receptor Mediates Cellular Degradation of Urokinase Receptor-Bound Complexes. J. Biol. Chem., 267: 14543–14546, 1992.

37. Skriver, L., Larsson, L. I., Kielberg, V., Nielsen, L. S., Andresen, P. B., Kristensen, P., and Danø, K. Immunocytochemical Localization of Urokinase-Type Plasminogen Activator in Lewis Lung Carcinoma. J. Cell Biol., 99: 753–758, 1984.

38. Kristensen, P., Eriksen, J., Blasi, F., and Danø, K. Two Alternatively Spliced Mouse Urokinase Receptor mRNAs with different Histological Localization in the Gastrointestinal Tract. J. Cell Biol., 115: 1763–1771, 1991.

39. Kristensen, P., Pyke, C., Lund, L. R., Andreasen, P. A., and Danø, K. Plasminogen activator inhibitor-type 1 in Lewis lung carcinoma. Histochemistry, 93: 559–566, 1990.

40. Grøndahl-Hansen, J., Ralfkiær, E., Kirkeby, L. T., Kristensen, P., Lund, L. R., and Danø, K. Localization of Urokinase-type Plasminogen Activator in Stromal Cells in Adenocarcinomas of the Colon in Humans. Amer. J. Pathol., 138: 111–117, 1991.

41. Pyke, C., Kristensen, P., Ralfkiær, E., Grøndahl-Hansen, J., Eriksen, J., Blasi, F., and Danø, K. Urokinase-type Plasminogen Activator Is Expressed in Stromal Cells and Its Receptor in Cancer Cells at Invasive Foci in Human Colon Adenocarcinomas. Amer. J. Pathol., 138: 1059–1067, 1991.

42. Pyke, C., Kristensen, P., Ralfkiær, E., Eriksen, J., and Danø, K. The Plasminogen Activation System in Human Colon Cancer: Messenger RNA for the Inhibitor PAI-1 Is Located in Endothelial Cells in the Tumor Stroma. Cancer Research, 51: 4067–4071, 1991.

43. Pyke, C., Ralfkiær, E., Rønne, E., Grøndahl-Hansen, J., Høyer-Hansen, G., Brünner, N., Græm, N., Tryggvason, K., and Danø, K. mRNA for Some of the Components of the uPA Pathway of Plasminogen Activation is Located in Non-Malignant Cells in the Tumor Stroma at Invasive Foci in Human Cancer. Proc. third Int. Workshop on the Molecular and Cellular Biology of Plasminogen Activation,Elsinore,p. 45, 1991.

44. Sappino, A. P., Belin, D., Huarte, J., Hirschelscholz, S., Saurat, J. H., and Vassalli, J. D. Differential protease expression by cutaneous squamous and basal cell carcinomas. J. Clin. Invest., 88: 1073–1079, 1991.

45. Pyke, C., Græm, N., Ralfkiær, E., Rønne, E., Høyer-Hansen, G., Brünner, N., and Danø, K. Receptor for Urokinase is Present in Tumor-associated Macrophages in Ductal Breast Carcinoma. Cancer Research, 53: 1–5, 1993.

46. Basset, P., Wolf, C., and Chambon, P. Expression of the Stromelysin-3 Gene in Fibroblastic Cells of Invasive Carcinomas of the Breast and other Human Tissues: A Review. Breast Cancer Res. Treat., 24: in press, 1992.

47. Reilly, D., Christensen, L., Duch, M., Nolan, N., Duffy, M. J., and Andreasen, P. A. Type-1 Plasminogen Activator Inhibitor in Human Breast Carcinomas. Int. J. Cancer, 50: 208–214, 1992.

48. Basset, P., Bellocq, J. P., Wolf, C., Stoll, I., Hutin, P., Limacher, J. M., Podhajcer, O. L., Chenard, M. P., Rio, M. C., and Chambon, P. A Novel metalloproteinase gene specifically expressed in stromal cells of breast carcinomas. Nature, 348: 699–704, 1990.

49. Pyke, C., Ralfkiær, E., Tryggvason, K., and Danø, K. Messenger RNA for two type IV collagenases is located in non-malignant stromal cells in human colon cancer. Amer. J. Pathol., in press: 1992.

50. Pyke, C., Ralfkiær, E., Huhtala, P., Hurskainen, T., Danø, K., and Tryggvason, K. Localization of Messenger RNA for Mr 72,000 and 92,000 Type IV Collagenases in Human Skin Cancers by in Situ Hybridization. Cancer Research, 52: 1336–1341, 1992.

51. Poulsom, R., Pignatelli, M., Stetler-Stevenson, W. G., Liotta, L. A., Wright, P. A., Jeffery, R. E., Longcroft, J. M., Rogers, L., and Stamp, G. W. H. Stromal Expression of 72 kda Type IV Collagenase (MMP-2) and TIMP-2 mRNAs in Colorectal Neoplasia. Amer. J. Pathol., 141: 389–396, 1992.

52. Tryggvason, K., Höyhtyä, M., and Pyke, C. Type IV Collagenases in Invasive Tumors. Breast Cancer Res. Treat., 1992. (in press)

53. Danø, K., Grøndahl-Hansen, J., Eriksen, J., Nielsen, B. S., Rømer, J., and Pyke, C. The Receptor for Urokinase Plasminogen Activator. Stromal Cell Involvement in Extracellular Proteolysis During Cancer Invasion. Manuscript for Proteolysis and Protein Turnover,A. J. Barrett and J. Bond (eds.), Portland Press,London., 1992.

54. Duffy, M. J., O'Grady, P., Devaney, D., O'Siorain, L., Fennelly, J. J., and Lijnen, H. J. Urokinase-Plasminogen Activator, A Marker for Aggressive Breast Carcinomas. Cancer, 62: 531–533, 1988.

55. Duffy, M. J., Reilly, D., O'Sullivan, C., O'Higgins, N., Fennelly, J. J., and Andreasen, P. Urokinase-Plasminogen Activator, a New and Independent Prognostic Marker in Breast Cancer. Cancer Research, 50: 6827–6829, 1990.
56. Jänicke, F., Schmitt, M., Hafter, R., Hollrieder, A., Babic, R., Ulm, K., Gössner, W., and Graeff, H. Urokinase-type Plasminogen Activator (uPA) Antigen is a Predictor of Early Relapse in Breast Cancer. Fibrinolysis, 4: 69–78, 1990.
57. Jänicke, F., Schmitt, M., and Graeff, H. Clinical Relevance of the Urokinase-Type and Tissue-Type Plasminogen Activators and of Their Type 1 Inhibitor in Breast Cancer. Semin. Thromb. Hemostasis, 17: 303–312, 1991.
58. Grçndahl-Hansen, J., Christensen, I. J., Rosenquist, C., Brünner, N., Blichert-Toft, M., Mouridsen, H. T., and Danø, K. High Levels of uPA and PAI-1 From Breast Cancer Tissue are Associated with Poor Prognosis. Proc. Amer. Ass. Cancer Res., 33: 362, 1992. (Abstract)
59. Rosenquist, C., Thorpe, S. M., Danø, K., and Grøndahl-Hansen, J. Enzyme-linked Immunosorbent Assay of Urokinase-type Plasminogen Activator (uPA) in Cytosolic Extracts of Human Breast Cancer Tissue. Submitted, 1992.
60. Foekens, J. A., Schmitt, M., van Putten, W. L. J., Peters, H. A., Bontenbal, M., Jänicke, F., and Klijn, J. G. M. Prognostic Value of Urokinase-type Plasminogen Activator in 671 Primary Breast Cancer Patients. Cancer Research, 52: 6101–6105, 1992.
61. Ellis, V., Wun, T. C., Behrendt, N., Rçnne, E., and Danø, K. Inhibition of Receptor-bound Urokinase by Plasminogen-activator Inhibitors. J. Biol. Chem., 265: 9904–9908, 1990.
62. Lipford, III. E. H., Eggleston, J. C., Lillemoe, K. D., Sears, D. L., Moore, G. W., and Baker, R. R. Prognostic Factors in Surgically Resected Limited-stage, Nonsmall Cell Carcinoma of the Lung. Am. J. Surg. Pathol., 8: 357–365, 1984.
63. Mountain, C. F., Lukeman, J. M., Hammar, S. P., Chamberlain, D. W., Coulson, W. F., Page, D. L., Victor, T. A., and Weiland, L. H. Lung Cancer Classification: The Relationship of Disease Extent and Cell Type to Survival in a Clinical Trials Population. J. Surg. Oncol., 35: 147–156, 1987.
64. Sørensen, J. B. and Badsberg, J. H. Prognostic Factors in Resected Stages I and II Adenocarcinoma of the Lung. J. Thorac. Cardiovasc. Surg., 99: 218–226, 1990.
65. Cox, D. R. Regression models and life tabels (with discussion). J. R. Statist. Soc., 187: 187–220, 1972.
66. Nielsen, L. S., Grøndahl-Hansen, J., Andreasen, P. A., Skriver, L., Zeuthen, J., and Danø, K. Enzyme-Linked Immunosorbent Assay for Human Urokinase-Type Plasminogen Activator and its Proenzyme using a Combination of Monoclonal and Polyclonal Antibodies. J. Immunoassay, 7: 209–228, 1986.
67. Brünner, N., Thompson, E. W., Spang-Thomsen, M., Rygaard, J., Danø, K., and Zwiebel, J. A. lacZ Transduced Human Breast Cancer Xenografts as an in vivo Model for the Study of Invasion and Metastasis. Eur. J. Cancer, 28A: 1989–1995, 1992.
68. Frandsen, T. L., Boysen, B. E., Jirus, S., Zwiebel, J., Spang-Thomsen, M., and Brunner, N. Assays for the Study of Human Cancer Cell Invasion and Metastasis. Fibrinolysis, 6: 71–76, 1992.
69. Brünner, N., Boysen, B., Rømer, J., and Spang-Thomsen, M. The Nude Mouse as in Vivo Model for Human Breast Cancer Invasion and Metastasis. Breast Cancer Res. Treat., 24: 257–264, 1993.
70. Kristensen, P., Eriksen, J., and Danø, K. Localization of urokinase-type plasminogen activator messenger RNA in the normal mouse by in situ hybridization. J. Histochem. Cytochem. 1991, 39: 341–349.
71. Quax, P. H. A., van uijen, G. N. P., Weening-Verhoeff, E. J. D., Lund, L. R., Danø, K., Ruiter, D. J., and Verheijen, J. H. Metastatic behaviour of human melanoma cell lines in nude mice correlates with urokinase-type plasminogen activator, its type-1 inhibitor and urokinase mediated matrix-degraradation. J. Cell Biol. 1991, 115: 191–199.
72. Pöllänen, J., Hedman, K., Nielsen, L. S., Danø, K., and Vaheri, A. Ultrastructural localization of plasma membrane-associated urokinase-type plasminogen activator at focal contacts. J. Cell Biol. 1988, 106:87–95.
73. Jin, L., Nakajima, M., and Nicolson, G. L. Immunochemical localization of heparanase in mouse and human melanomas. Int. J. Cancer 1990, 45:1088–1095.
74. Liotta, L. A., Steeg, P. S., and Stetler-Stevenson, W. G. Cancer metastasis and angiogenesis: an imbalance of positive and negative regulation. Cell 1991, 64:327–336.
75. Tryggvason, K., Hoyhtya, M., and Salo, T. Proteolytic degradation of extracellular matrix in tumor invasion. Biochem. Biophys. Acta 1987, 907:191–217.
76. Rochefort, H., Augereau, P., Brioszzo, P., Capony, F., Cavailles, V., Freiss, G., Garcia, M., Maudelonde, T., Morisset, M., Touitou, I., and Vignon, F. Oestrogen-induced procathepsin D in breast cancer: from biology to clinical applications. Proc. R. Soc. Edinb. Sect. B (Biol.) 1989, 95:107–118.
77. Pepper, M.S., Sappino, A. P., Montesano, R., Orci, L., and Vassalli, J. D. Plasminogen activator inhibitor-1 is induced in migrating endothelial cells. J. Cell Physiol. 1992, 153:129–139.
78. Grøndahl-Hansen, J., Christensen, I. J., Rosenquist, C., Brünner, N., Mouridsen, H. T., Danø, K., and Blicher-Toft, M. High levels of Urokinase-type Plasminogen Activatro and Its inhibitor PAI-1 in Cytosolic Extracts fo Breast Carcinomas are Associated with Poor Prognosis. Cancer Research, 1993, 53: 2513–2521.
79. Fujiwara, K., Saita T., Takenawa N., Matsumoto N. Kitagawa T. Enzyme-linked Immunosorbent Assay for the Quantification of Actinomycin D Using β-galactosidase as a Label. Cancer Research, 1988, 48: 4843–4847.
80. Åqvist J., Medina C. and Samuelsson J. E., A new method for predicting binding affinity in computer-aided drug design. Protein Eng., 1994, 7: 385–391.
81. Scott, J. K. and Smith, G. P. Searching for peptide ligands with an epitope library. Science, 1991, 249: 386–390.
82. Smith, G. P. Surface presentation of protein epitopes using bacteriophage expression systems. Curr. Opin. Biotechnol., 1991, 2: 668–673.
83. Dower, W. J. Phage power. Current Biology, 1992, 2: 251–253.
84. Scott, J. K. Discovering peptide ligands using epitope libraries. Trends Biochem., 1992, 17: 241–245.
85. Parmley, S. F. and Smith, G. P. Antibody-selectable filamentous fd phage vectors: affinity purification of target genes. Gene, 1988, 73: 305–318.
86. Devlin, J. J. et al. Random peptides libraries: a source of specific protein binding molecules. Science, 1990, 249: 404–406.
87. Hammer, J. et al. Identification of HLA-DR1 binding peptides using M13 display libraries. J. Exp. Med., 1992, 176: 1007–13.
88. Oldenburger, K. R. et al. Peptides ligands for a sugar-binding protein isolated from a random peptide library. PNAS, 1992, 88: 5393–97.

89. Barbas, C. F. et al. Assembly of combinatorial antibody libraries on phage surfaces: the gene III site. PNAS, 1991, 88: 7978–82.
90. Kang, A. S. et al. Linkage of recognition and replication functions by assembly combinatorial antibody Fab libraries along phage surfaces. PNAS, 1991, 88: 4363–66.
91. Pannekoek, H. et al. Functional display of human plasminogen-activator inhibitor 1 (PAI-1) on phages: novel perspectives for structure-function analysis by error-prone DNA synthesis. Gene, 1993, 128: 135–140.
92. Horn, I et al. Epitope mapping of an anti-$\alpha_2$MR/LRP monoclonal antibody using a bacteriophage displayed $\alpha_2$MR/LRP random fragment library. In: Leukocyte typing V: white cell differentiation antigens: Oxford University Press, Oxford, Todd III, R. F. et al. (eds.) (in press).
93. Eichler, J. and Hougten, R. A. Identification of substrate-analog trypsin inhibitors through the screening of synthetic peptide combinatorial libraries. Biochemistry, 1993, 32: 11035–11041.

What is claimed is:

1. A method of inhibiting malignant tumour growth, invasion and/or metastasis in a patient, the method comprising
suppressing the inhibitory activity of an inhibitor of a protease in malignant tumour tissue,
where said inhibitor being Plasminogen Activator Inhibitor I (PAI-1), said inhibitor is one whose inhibitory activity promotes malignant tumor growth, invasion and/or metastasis,
where said suppressing is effected by exposing said inhibitor to a tumor-inhibiting amount of a suppressor of said inhibitor,
whereby malignant tumor growth, invasion and/or metastasis is inhibited.

2. A method according to claim 1, wherein as a result of the suppression of the inhibitor activity of an inhibitor of a protease in malignant tumour tissue, the protease degrades the malignant tumour tissue.

3. A method according to claim 1, wherein the suppression of the inhibitory activity of an inhibitor of a protease in malignant tumour tissue results in interference with the process of tumour angiogenesis, said process being one promoted by said protease inhibitor.

4. A method according to claim 1, wherein the suppression of the inhibitory activity of an inhibitor of a protease in malignant tumour tissue results in interference with the migrating capacity of malignant tumour cells or of other cells in the tumour stroma.

5. A method according to claim 1, wherein the patient is a patient who has been established to have a carcinoma in situ.

6. A method according to claim 1, wherein the patient is a patient who has been established to have a high risk of developing a malignant tumour by having a high-risk-indicating score of a tumour marker.

7. A method according to claim 1, wherein the patient is a patient who has an increased concentration of the inhibitor of the protease in the malignant tumour tissue and/or in plasma and/or serum.

8. A method according to claim 1, wherein the patient is a patient who has an increased concentration of the inhibitor of the protease in the malignant tumor tissue and/or in plasma and/or serum, and the increased concentration of the inhibitor of the protease has been established to be a prognostic factor indicating a poor prognosis for the patient having the type of malignant tumour in question.

9. A method according to claim 1, wherein the patient is a patient who has an increased concentration of the inhibitor of the protease in the malignant tumor tissue and/or in plasma and/or serum, and the increased concentration of the inhibitor of the protease may be established to be a predictive factor indicating efficiency of the treatment of the type of malignant tumour in question by suppressing the said inhibitor.

10. A method according to claim 1, wherein the malignant tumour is selected from the group consisting of mammary carcinomas, urological carcinomas e.g. prostate carcinoma and bladder carcinoma, gynaecological carcinomas, non-small cell lung tumours, gastrointestinal cancers, brain tumours, sarcomas, haematological malignancy and skin cancers.

11. A method according to claim 1, wherein the suppression of the inhibitory activity of the inhibitor of the protease is obtained by administering to the patient a compound which suppresses the inhibitory activity of the inhibitor of the protease.

12. A method according to claim 1, wherein the compound is a suppressor which suppresses the plasminogen activator-inhibitory activity of PAI-1 by inhibiting the binding of PAI-1 to vitronectin.

13. A method according to claim 1, wherein the suppressor is a compound which inhibits the u-PA inhibiting effect of PAI-1, but does not inhibit the binding of uPA to uPAR.

14. A method according to claim 1, wherein the compound is a suppressor which is capable of binding to PAI-1 and not capable of converting plasminogen into plasmin.

15. A method according to claim 1, wherein the suppressor is selected from the group consisting of an antibody which is capable of binding to PAI-1, and an Antigen Binding fragment thereof.

16. A method according to claim 1, wherein the suppressor which is capable of binding to PAI-1 has a cytotoxic drug coupled thereto.

17. A method according to claim 6 wherein the tumour marker is a serum and/or plasma marker.

18. The method of claim 1, the method being performed prior to surgery to remove malignant tumor tissue.

19. The method of claim 1, the method being performed after surgery to remove malignant tumor tissue.

20. The method of claim 1 wherein malignant tumor growth is inhibited.

21. The method of claim 1 wherein malignant tumor invasiveness is inhibited.

22. The method of claim 1 wherein malignant tumor metastasis is inhibited.

23. The method of claim 1 wherein the malignant tumor is not a skin cancer.

24. A method of inhibiting malignant tumor growth, invasion and/or metastasis in a patient, the method comprising
inhibiting the activity of plasminogen activator inhibitor 1 PAI-1 in promoting malignant tumor growth, invasion and/or metastasis,
where said inhibiting is effected by exposing said PAI-1 to a tumor-inhibiting amount of an inhibitor of said PAI-1,
whereby malignant tumor growth, invasion and/or metastasis is inhibited.

* * * * *